(12) United States Patent
Perreaut et al.

(10) Patent No.: US 7,842,806 B2
(45) Date of Patent: Nov. 30, 2010

(54) PYRIDOPYRIMIDONE DERIVATIVES, PREPARATION THEREOF, THERAPEUTIC USE THEREOF

(75) Inventors: Pierre Perreaut, Saint-Clement-de-Riviere (FR); Samir Jegham, Montferrier-sur-Lez (FR); Bernard Bourrie, Saint-Gely-du-Fesc (FR); Pierre Casellas, Montpellier (FR); Jean-Robert Labrosse, St. Hilaire de Beauvoir (FR); Florence Durand, Aniane (FR)

(73) Assignee: sanofi-aventis, Paris (FR)

(*) Notice: Subject to any disclaimer, the term of this patent is extended or adjusted under 35 U.S.C. 154(b) by 155 days.

(21) Appl. No.: 12/166,431

(22) Filed: Jul. 2, 2008

(65) Prior Publication Data
US 2009/0048277 A1 Feb. 19, 2009

Related U.S. Application Data

(63) Continuation of application No. PCT/FR2007/000050, filed on Jan. 12, 2007.

(30) Foreign Application Priority Data
Jan. 13, 2006 (FR) .................................. 06 00298

(51) Int. Cl.
C07D 471/00 (2006.01)
(52) U.S. Cl. ...................................................... 544/279
(58) Field of Classification Search .................. 544/279
See application file for complete search history.

(56) References Cited

U.S. PATENT DOCUMENTS

| | | | |
|---|---|---|---|
| 3,534,039 A | 10/1970 | Davoll | |
| 5,620,981 A | 4/1997 | Blankley et al. | |
| 5,733,913 A | 3/1998 | Blankley et al. | |
| 5,733,914 A | 3/1998 | Blankley et al. | |
| 5,952,342 A | 9/1999 | Blankley et al. | |
| 2007/0167469 A1 | 7/2007 | Bourrie | |

FOREIGN PATENT DOCUMENTS

| | | | |
|---|---|---|---|
| EP | 0 790 997 B1 | | 3/2000 |
| WO | WO 96/15128 | | 5/1996 |
| WO | WO 96/34867 | * | 11/1996 |
| WO | WO 01/21577 A2 | | 3/2001 |
| WO | WO 01/55147 | | 8/2001 |
| WO | WO 01/70741 A1 | | 9/2001 |
| WO | WO 02/12238 A2 | | 2/2002 |
| WO | WO 03/000011 | | 1/2003 |
| WO | WO 2004/063195 A1 | | 7/2004 |
| WO | WO 2004/085436 | | 10/2004 |
| WO | WO 2005/105097 A2 | | 11/2005 |
| WO | WO 2006/007693 A1 | | 1/2006 |
| WO | WO 2006/016067 A2 | | 2/2006 |
| WO | WO 2007/003765 | | 1/2007 |

OTHER PUBLICATIONS

U.S. Appl. No. 11/955,583, filed Dec. 13, 2007, Bourrie.
Alam, Fighting Cancer: 'Magic Bullets' on Target to Lead Market, Pharmalicensing.com (Mar. 8, 2005).
Anzali et al, 1. Endothelin antagonists: Search for Surrogates of Methylendioxyphenyl by Means of a Kohonen Neural Network, Bioorganic & Medicinal Chemistry Letters 8 (1998) pp. 11-16.
Lewell et al, Drug Rings Database with Web Interface. A Tool for Identifying Alternative Chemical Rings in Lead Discovery Programs, J. Med. Che. 2003, 46, pp. 3257-3274.
Mederski et al, 2. Endothelin Antagonists: Evaluation of 2,1,3-Benzothiadiazole as a Methylendioxyphenyl Bioisoster, Bioorganic & Medicinal Chemistry Letters 8 (1998) pp. 17-22.
Palmer et al, Structure-activity Relationships for 2-anilino-6-phenylpyrido[2,3-d]pyrimidin-7(8H)-ones as Inhibitors of the Cellular Checkpoint Kinase Wee1, Bioorganic & Medicinal Chemistry Letters 15 (2005) pp. 1931-1935.
Schroeder et al, Soluble 2-Substituted Aminopyrido[2,3-d]primidin-7-yl Ureas. Structure—Activity Relationships against Selected Tyrosine Kinases and Exploration of in Vitro and in Vivo Anticancer Activity, J. Med. Chem., 2001, 44, 1915-1926.
Sicinski, Killer Breast Cancer Therapy Hope, BBC News/Health Jan. 21, 2006.
Thompson et al, Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receiptor-1 and Vascular Endothelial Growth Factor Receptor-2 Tyrosine Kinases, J. Med. Chem., 2005,48, 4628-4653.

(Continued)

*Primary Examiner*—Michael G Hartley
*Assistant Examiner*—Shirley V Gembeh
(74) *Attorney, Agent, or Firm*—Kelly L. Bender

(57) ABSTRACT

The disclosure relates to pyrido[2,3-d]pyrimidone compounds, to the preparation thereof and to the therapeutic use thereof, wherein said compounds are of general formula (I):

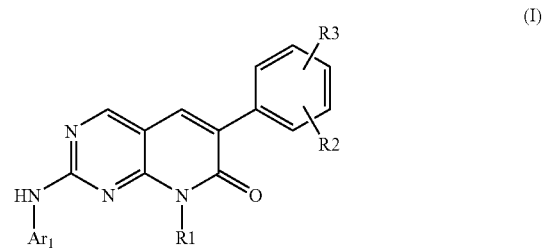

(I)

in the form of a base or of an addition salt with an acid which is pharmaceutically acceptable, in the form of hydrates or of solvates, and also in the form of enantiomers, diastereoisomers and a mixture thereof. The disclosure also relates to processes for preparing said compounds, to pharmaceutical compositions containing a compound of general formula (I), and to the therapeutic use of said compounds and compositions.

22 Claims, No Drawings

OTHER PUBLICATIONS

Walsh, No 'Magic Bullet' Cure for Cancer, BBC News, International Version, Medical Notes, Feb. 1, 2007.

Albrecht, Untersuchungen uber die antibakterielle Aktivitat von Chinoloncarbonsauren. VI (1). Der Einfluss von kondensierten Funfringen and 1-Substituenten, Eur. J. Med. Chem.-Chimica Therapeutica, 1977 (12) 3 pp. 231-235.

Carmichael et al, Evaluation of a Tetrazolium-based Semiautomated Colorimetric Assay: Assessment of Chemosensitivity Testing, Cancer Research, 1987 (47) pp. 936-942.

Clark et al, Synthesis and Analgesic Activity of 1,3-Dihydro-3-(substituted phenyl)imidazo[4,5-b]pyridin-2-ones and 3-(Substituted phenyl)-1,2,3-triazolo[4,5-b]pyridines, J. Med. Chem., 1978 (21) 9 pp. 965-978.

Colomb et al, Nuclear Texture Parameters as Discriminant Factors in Cell Cycle and Drug Sensitivity Studies, Cytometry, 1991 (12) pp. 15-25.

Drexler, Leukemia Cell Lines: in vitro Models for the Study of Chronic Myeloid Leukemia, Leukemia Research, 1994 (12) 12 pp. 919-927.

El Hadri et al, New Series of N-substituted Phenyl Ketone Oxime Ethers: Synthesis and Bovine Beta3-adrenergic Agonistic Activities, Pharmazie, 2003 (58) pp. 13-17.

Fujishita, et al, Sensitivity of Non-Small-Cell Lung Cancer Cell Lines Established from Patients Treated with Prolonged Infusions of Paclitaxel, Oncology, 2003 (64) pp. 399-406.

Klutchko et al, 2-Substituted Aminopyrido[2,3-d]pyrimidin-7(8H)-ones. Structure-Activity Relationships Against Selected Tyrosine Kinases and in Vitro and in Vivo Anticancer Activity, J. Med. Chem., 1988 (41) pp. 3276-3292.

Koeffler et al, An Undifferentiated Variant Derived From the Human Acute Myelogenous Leukemia Cell Line (KG-1), Blood, 1980 (56) 2 pp. 265-273.

Kuriyama et al, CLM-T1: A Cell Line Derived From T-Lymphocyte Acute Phase of Chronic Myelogenous Leukemia, Blood, 1989 (74) 4 pp. 1381-1387.

Lozzio et al, Brief Communication: Cytotoxicity of a Factor Isolated From Human Spleen, J Natl Cancer hist, 1973 (50) pp. 535-538.

Lozzio et al, Human Chronic Myelogenous Leukemia Cell-line with Positive Philadelphia Chromosome, Blood, 1975 (45) pp. 321-334.

Soda et al, Lymphoid Crisis with T-cell Phenotypes in a Patient with Philadelphia Chromosome Negative Chronic Myeloid Leukaemia, British Journal of Haematology, 1985 (59) pp. 671-679.

Westphal et al, Epidermal Growth Factor Receptors in the Human Glioblastoma Cell Line SF268 Differ From Those in Epidermoid Carcinoma Cell Line A431, Biochemical and Biophysical Research Comm., 1985 (132) 1 pp. 284-289.

Willard et al, Potential Diuretic—Beta-Adrenergic Blocking Agents: Synthesis of 3-[2[(1,1-Dimethylethyl) amino]-1-hydroxyethyl]-1,4-dioxino[2,3-g]quinolines, J. Org. Chem., 1981 (46) 19 pp. 3846-3852.

* cited by examiner

PYRIDOPYRIMIDONE DERIVATIVES, PREPARATION THEREOF, THERAPEUTIC USE THEREOF

A subject matter of the present invention is pyrido[2,3-d] pyrimidone derivatives, their preparation and their therapeutic application.

Compounds derived from pyrido[2,3-d]pyrimidone are described in patent application WO 96/34867 and patent U.S. Pat. No. 5,620,981. These compounds are potentially useful in treating disorders of cell proliferation.

According to a first aspect, a subject matter of the present invention is compounds corresponding to the formula (I):

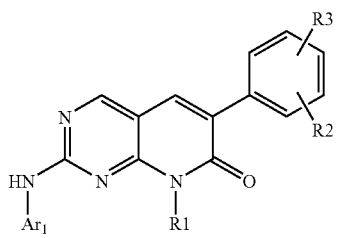

(I)

in which:
R1 is selected from the group consisting of: H, $(C_1-C_6)$ alkyl, $(C_2-C_6)$alkenyl, $(C_2-C_6)$alkynyl, $(C_3-C_7)$cycloalkyl and $(C_3-C_7)$cycloalkyl $(C_1-C_6)$alkyl;

R2 and R3 are independently selected from the group consisting of: H, halogen, $(C_1-C_4)$alkyl, trifluoromethyl and $(C_1-C_4)$alkoxy;

Ar₁ represents a radical chosen from:

a) 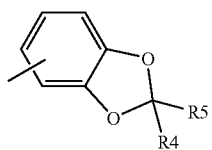

b) 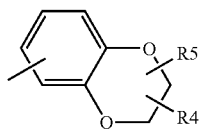

c) 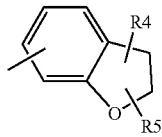

d) 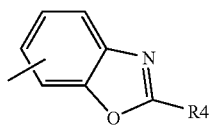

e) 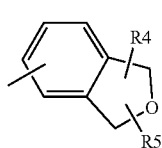

f) 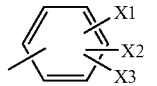

g) 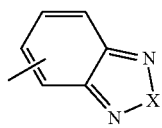

R5 is selected from the group consisting of: H, cyano, hydroxy$(C_1-C_4)$alkyl, $(C_1-C_6)$alkoxy$(C_1-C_4)$alkyl, —$(CH_2)_n$NR6R7, —$(CH_2)_m$CO₂R6, —$(CH_2)_m$CONHNR6R7, —$(CH_2)_m$CONR6R7, —$(CH_2)_m$CONR7OR8, —$(CH_2)_n$NR6COR7 and —$(CH_2)_n$NR6COOR7;

R4 is selected from the group consisting of: H, $(C_1-C_4)$ alkyl and R5;

it being understood that, when Ar₁ takes the value a), then R4 and R5 are not two hydrogen atoms;

R6 and R7 are independently selected from the group consisting of: H, $(C_1-C_4)$alkyl, $(C_3-C_7)$cycloalkyl and $(C_3-C_7)$cycloalkyl$(C_1-C_4)$alkyl; R7 can also represent a tert-butoxycarbonyl or benzyloxycarbonyl group;

or R6 and R7, together with the nitrogen atom to which they are bonded, constitute an azetidinyl, pyrrolidinyl, piperidinyl, piperazinyl or morpholinyl radical;

R8 is selected from the group consisting of: H and $(C_1-C_4)$ alkyl;

X is O or S;

X1 and X2 are independently selected from the group consisting of: H and —$(C_1-C_6)$alkyl-N$((C_1-C_6)$alkyl$)_2$;

when one of X1 and X2 is other than H, then X3 is selected from the group consisting of: hydroxyl and $(C_1-C_6)$alkoxy;

when X1 and X2 are H, then X3 is selected from the group consisting of: —$(CH_2)_n$—CH(NHR9)-CO—R10, —O—$(CH_2)_n$—CH(NHR9)-CO—R10 and —NHSO₂—$(C_1-C_6)$ alkyl;

R9 is selected from the group consisting of: H, t-butyloxycarbonyl, benzyloxycarbonyl and $(C_1-C_6)$alkyl;

R10 is selected from the group consisting of: hydroxyl, $(C_1-C_6)$alkoxy and —NR11R12;

R11 and R12 are independently selected from the group consisting of: H and $(C_1-C_6)$alkyl; or R11 and R12, together with the nitrogen atom to which they are bonded, constitute an azetidinyl, pyrrolidinyl, piperidinyl, piperazinyl or morpholinyl radical;

m represents 0, 1, 2 or 3;

n represents 1, 2 or 3;

in the base form or in the form of an addition salt with an acid, and also in the hydrate or solvate form.

The compounds of formula (I) can exist in the form of bases or of addition salts with acids. When compounds of formula (I) comprise free acid functional groups, for example carboxylic, sulfonic or phosphonic acid functional groups, these acid functional groups can be salified using bases in order to form addition salts. Such addition salts form part of the invention.

The addition salts with acids or with bases are advantageously prepared with, respectively, pharmaceutically acceptable acids or bases but the salts of other acids or bases, for example of use in the purification or isolation of the compounds of formula (I), also form part of the invention.

The compounds of formula (I) can also exist in the form of hydrates or solvates, namely in the form of combinations or associations with one or more molecules of water or with a solvent. Such hydrates and solvates also form part of the invention.

The compounds of formula (I) can comprise one or more asymmetric carbon atoms. The non-chiral form or the racemic form or the form enriched in a stereoisomer or the form enriched in an enantiomer form part of the invention.

In the context of the present invention:
the term "a halogen atom" is understood to mean: a fluorine, a chlorine, a bromine or an iodine;
the term "an alkyl group" is understood to mean: a saturated, linear or branched, aliphatic group. Mention may be made, by way of example, of the methyl, ethyl, n-propyl, n-butyl, n-pentyl, n-hexyl, n-heptyl, 1-methylethyl, 1-methylpropyl, 2-methylpropyl, 1,1-dimethylethyl, 1-methylbutyl, 2-methylbutyl, 3-methylbutyl, 1,1-dimethylpropyl, 1,2-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methyl-propyl, 1-ethyl-2-methylpropyl, 1-ethylbutyl, 2-ethylbutyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 1,1,2,2-tetramethylpropyl, 1-ethylpentyl, 2-ethylpentyl, 3-ethylpentyl, 1-ethyl-1-methylbutyl, 1-ethyl-2-methylbutyl, 1-ethyl-3-methylbutyl, 2-ethyl-1-methylbutyl, 2-ethyl-2-methylbutyl, 2-ethyl-3-methylbutyl, 1-propylbutyl, 1-(1-methylethyl)butyl or 1-(1-methylethyl)-2-methylpropyl groups;
the term "an alkenyl group" is understood to mean: a mono- or polyunsaturated, linear or branched, aliphatic group comprising, for example, one or two ethylenic unsaturations;
the term "an alkynyl group" is understood to mean: a mono- or polyunsaturated, linear or branched, aliphatic group comprising, for example, one or two acetylenic unsaturations;
the term "a cycloalkyl group" is understood to mean: cyclopropyl, cyclobutyl, cyclopentyl, cyclohexyl, cycloheptyl, bicyclo[2.2.1]heptyl, cyclooctyl, bicyclo[2.2.2]octyl, bicyclo[3.2.1]octyl or adamantyl.

Mention may be made, among the compounds of formula (I) which are subject matters of the invention, of the compounds corresponding to the formula (I):

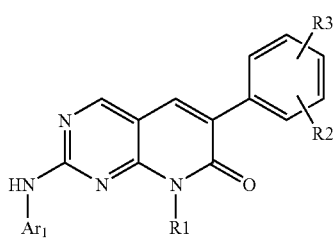

(I)

in which:
R1 is selected from a group consisting of H, $(C_1-C_6)$alkyl, $(C_3-C_7)$cycloalkyl, $(C_1-C_6)$alkyl$(C_3-C_7)$cycloalkyl, R2 and R3 are independently chosen from a halogen atom or a $(C_1-C_4)$alkyl, trifluoromethyl or $(C_1-C_4)$alkoxy group;

$Ar_1$ represents a radical chosen from:

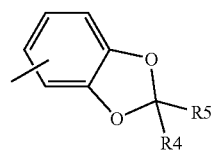

a)

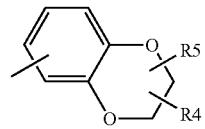

b)

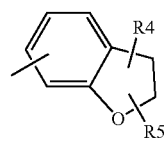

c)

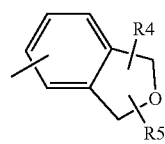

d)

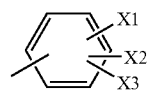

e)

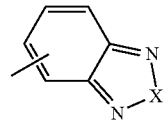

f)

R5 represents a hydrogen atom or a cyano, hydroxy$(C_1-C_4)$alkyl or $(C_1-C_6)$alkoxy$(C_1-C_4)$alkyl group or a $(CH_2)_n NR6R7$, $(CH_2)_m CO_2R6$, $(CH_2)_m CONHNR6R7$, $(CH_2)_m CONR6R7$, $(CH_2)_m CONR7OR8$, $(CH_2)_n NR6COR7$ or $(CH_2)_n NR6COOR7$ group;

R4 represents a hydrogen atom, a $(C_1-C_4)$alkyl group or one of the values of R5;

it being understood that, when $Ar_1$ takes the value a), then R4 and R5 are not two hydrogen atoms;

R6 and R7 represent, each independently of one another, a substituent chosen from H, $(C_1-C_4)$alkyl, $(C_3-C_7)$cycloalkyl or $(C_1-C_4)$alkyl$(C_3-C_7)$cycloalkyl; R7 can also represent a tert-butoxycarbonyl or benzyloxycarbonyl group;

or R6 and R7, together with the nitrogen atom to which they are bonded, constitute an azetidinyl, pyrrolidinyl, piperidinyl, piperazinyl or morpholinyl radical;

R8 represents a hydrogen atom or a $(C_1-C_4)$alkyl group;

X is O or S;

X1 and X2 are independently selected from the group consisting of H and —$(C_1-C_6)$alkyl-N$((C_1-C_6)$alkyl$)_2$;

when one of X1 and X2 is other than H, then X3 is selected from the group consisting of OH and O—$(C_1-C_6)$alkyl;

when X1 and X2 are H, then X3 is selected from the group consisting of: $(CH_2)_n$—CH(NHR9)—CO—R10, —O—$(CH_2)_n$—CH(NHR9)—CO—R10 and —NHSO$_2$—$(C_1$-$C_6)$alkyl;

R9 is chosen from H, t-butyloxycarbonyl, benzyloxycarbonyl and $(C_1$-$C_6)$alkyl;

R10 is chosen from OH, O—$(C_1$-$C_6)$alkyl and NR11R12;

R11 and R12 are independently selected from the group consisting of H and $(C_1$-$C_6)$alkyl; or R11 and R12, together with the nitrogen atom to which they are bonded, constitute an azetidinyl, pyrrolidinyl, piperidinyl, piperazinyl or morpholinyl radical;

m represents 0, 1, 2, or 3;

n represents 1, 2 or 3.

Mention may be made, among the compounds of formula (I) which are subject matters of the invention, of the preferred compounds where $Ar_1$ represents a radical chosen from:

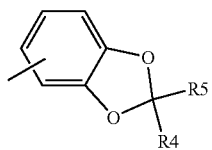 a)

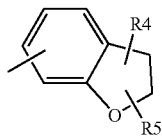 c)

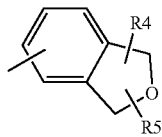 d)

 e)

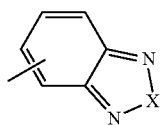 f)

in which R4, R5, X1, X2, X3 and X are as defined above, in the base form or in the form of an addition salt with an acid, and also in the hydrate or solvate form.

Among some products according to the invention, R1 is preferably a methyl. Among some products according to the invention, R1 is preferably a cyclopentyl. Among some products according to the invention, R1 is preferably a —CH$_2$—C≡CH group.

In the products according to the invention, R2 and R3 are preferably two chlorine atoms in the 2 and 6 positions.

Mention may be made, among the compounds of formula (I) which are subject matters of the invention, of the preferred compounds where $Ar_1$ represents the following radical:

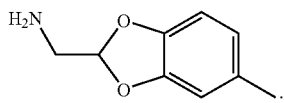

Mention may be made, among the compounds of formula (I) which are subject matters of the invention, of the preferred compounds where $Ar_1$ represents the following radical:

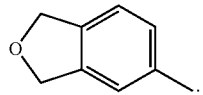

Mention may be made, among the compounds of formula (I) which are subject matters of the invention, of the preferred compounds where $Ar_1$ represents the following radical:

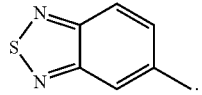

Mention may be made, among the compounds of formula (I) which are subject matters of the invention, of the preferred compounds where $Ar_1$ represents the following radical:

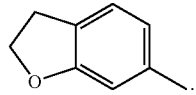

Mention may be made, among the compounds of formula (I) which are subject matters of the invention, of the preferred compounds where $Ar_1$ represents the following radical:

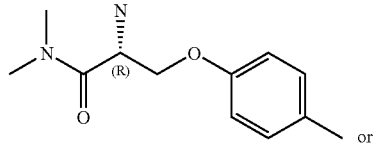 or

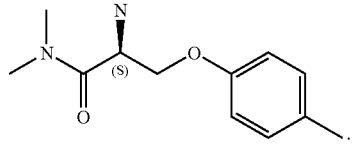

Mention may be made, among the compounds of formula (I) which are subject matters of the invention, of the preferred compounds where $Ar_1$ represents the following radical:

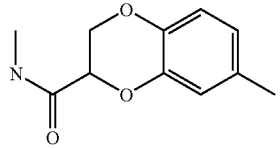

Mention may be made, among the compounds of formula (I) which are subject matters of the invention, of the preferred compounds where $Ar_1$ represents the following radical:

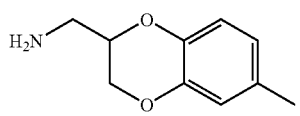

Mention may be made, among the compounds of formula (I) which are subject matters of the invention, of the preferred compounds where $Ar_1$ represents the following radical:

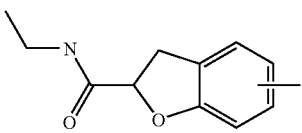

Mention may be made, among the compounds of formula (I) which are subject matters of the invention, of the preferred compounds where Ar₁ represents the following radical:

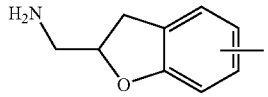

Mention may be made, among the compounds of formula (I) which are subject matters of the invention, of the preferred compounds where Ar₁ represents the following radical:

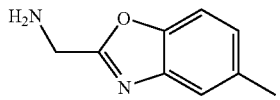

Mention may in particular be made, among the compounds of formula (I) of the invention, of the following compounds:
6-(2,6-dichlorophenyl)-2-[(1,3-dihydro-5-isobenzo-furanyl) amino]-8-methyl-8H-pyrido[2,3-d]pyrimidin-7-one,
(R/S)-2-[[2-(aminomethyl)-1,3-benzodioxol-5-yl]amino]-6-(2,6-dichlorophenyl)-8-methyl-8H-pyrido[2,3-d]pyrimidin-7-one,
2-(2,1,3-benzothiadiazol-5-ylamino)-6-(2,6-dichlorophenyl)-8-methyl-8H-pyrido[2,3-d]pyrimidin-7-one,
6-(2,6-dichlorophenyl)-2-[(2,3-dihydro-6-benzofuranyl) amino]-8-methyl-8H-pyrido[2,3-d]pyrimidin-7-one,
(2R)-2-amino-3-[4-[[6-(2,6-dichlorophenyl)-7,8-dihydro-8-methyl-7-oxopyrido[2,3-d]pyrimidin-2-yl]amino]phenoxy]-N,N-dimethylpropanamide,
(2S)-2-amino-3-[4-[[6-(2,6-dichlorophenyl)-7,8-dihydro-8-methyl-7-oxopyrido[2,3-d]pyrimidin-2-yl]amino]phenoxy]-N,N-dimethylpropanamide.

Mention may in particular be made, among the compounds of formula (I) of the invention, of the following compounds:
(R/S)-N-methylamide of 7-[6-(2,6-dichlorophenyl)-8-methyl-7-oxo-7,8-dihydropyrido[2,3-d]pyrimidin-2-ylamino]-2,3-dihydrobenzo[1,4]dioxin-2-carboxylic acid,
(R/S)-2-(2-aminomethyl-2,3-dihydrobenzo[1,4]dioxin-6-ylamino)-6-(2,6-dichlorophenyl)-8-methyl-8H-pyrido[2,3-d]pyrimidin-7-one,
(R/S)-N-ethylamide of 6-[6-(2,6-dichlorophenyl)-8-methyl-7-oxo-7,8-dihydropyrido[2,3-d]pyrimidin-2-ylamino]-2,3-dihydrobenzofuran-2-carboxylic acid,
(R/S)-N-ethylamide of 5-[6-(2,6-dichlorophenyl)-8-methyl-7-oxo-7,8-dihydropyrido[2,3-d]pyrimidin-2-ylamino]-2,3-dihydrobenzofuran-2-carboxylic acid,
(R/S)-2-(2-aminomethyl-2,3-dihydrobenzofuran-5-ylamino)-6-(2,6-dichlorophenyl)-8-methyl-8H-pyrido[2,3-d]pyrimidin-7-one,
(R/S)-2-(2-aminomethyl-2,3-dihydrobenzofuran-6-ylamino)-6-(2,6-dichlorophenyl)-8-methyl-8H-pyrido[2,3-d]pyrimidin-7-one,
2-(2,1,3-benzothiadiazol-5-ylamino)-8-cyclopentyl-6-(2,6-dichlorophenyl)-8H-pyrido[2,3-d]pyrimidin-7-one,
2-(2,1,3-benzothiadiazol-5-ylamino)-6-(2,6-dichlorophenyl)-8-(prop-2-ynyl)-8H-pyrido[2,3-d]pyrimidin-7-one,
2-(2-(aminomethyl)benzoxazol-5-ylamino)-6-(2,6-dichlorophenyl)-8-methyl-8H-pyrido[2,3-d]pyrimidin-7-one.

Another subject matter of the present invention relates to a process for the preparation of a compound of formula (I), characterized in that a compound of formula (II):

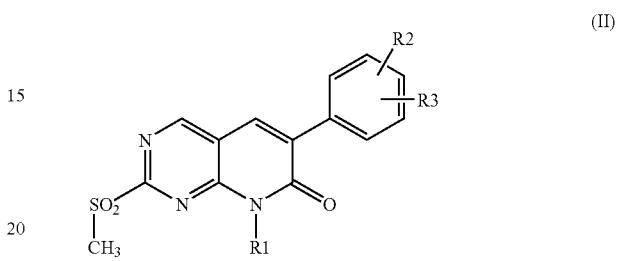

in which R1, R2 and R3 are as defined for (I), is reacted with an amine of formula Ar'₁NH₂ (III) in which Ar'₁ represents Ar₁, as defined for (I), or a precursor of Ar₁; if appropriate, the Ar'₁ group of the compound thus obtained is converted to an Ar₁ group.

The compounds of formula (II) are prepared by following the procedure described in J. Med. Chem., 1998, volume 41, pages 3276-3292. One of the compounds of formula (II), in which R1 is methyl and R2 and R3 are two chlorine atoms in the 2 and 6 positions, which is used for the synthesis of the products of examples 1 to 6, 8 to 12, 14 and 15, is 6-(2,6-dichlorophenyl)-8-methyl-2-methylsulfonyl-8H-pyrido[2,3-d]pyrimidin-7-one.

If appropriate, the amine functional groups present in the Ar'₁ group of the compound (III) are salified or protected by a protective group G beforehand.

The amines of formula (III) are known or available commercially or prepared by methods conventional in organic chemistry. Some preparations of the amines of formula (III) are known: from the corresponding nitro derivatives Ar'₁NO₂ (IV), by reduction either (i) in an acidic medium in the presence of a metal, such as iron or zinc in the powdered form, or (ii) with hydrogen in the presence of a catalyst, such as Pd/C.

Other amines of formula (III) are novel. In particular, the amines (R/S)-N-ethylamide of 6-amino-2,3-dihydrobenzofuran-2-carboxylic acid, (R/S)-N-ethylamide of 5-amino-2,3-dihydrobenzofuran-2-carboxylic acid, (R/S)-2-(N-Boc-aminomethyl)-2,3-dihydrobenzofuran-5-ylamine, (R/S)-2-(N-aminomethyl)-2,3-dihydrobenzofuran-5-ylamine, (R/S)-2-(N-Boc-aminomethyl)-2,3-dihydrobenzofuran-6-ylamine and (R/S)-2-(N-aminomethyl)-2,3-dihydrobenzofuran-6-ylamine, of use as intermediates, are a subject matter of the present invention, as are their processes of preparation.

The compounds of formula (IV) are known or prepared by known methods.

Thus, 5-nitro-1,3-benzodioxoles monosubstituted in the 2 position by a group R5=methoxycarbonyl can be prepared by the reaction of methyl dichloroacetate with 4-nitrocatechol (4-nitrobenzene-1,2-diol).

5-Nitro-1,3-benzodioxoles gem-disubstituted in the 2 position can be prepared according to Pharmazie, 2003, 58 (1), 13-17, by the reaction of ethyl dibromomalonate with 4-nitrocatechol (4-nitrobenzene-1,2-diol).

7-Nitro-2,3-dihydro-1,4-benzodioxins substituted in the 2 or 3 position by R5 and R4 can be prepared according to the method described in patent application WO 01/021577 starting from 4-nitrocatechol or by known chemical transformations.

(1,3-Dihydro-5-isobenzofuranyl)amine is described in J. Med. Chem., 1978, 21, 965-978.

2,3-Dihydro-1-benzofuran-6-amine is described in Eur. J. Med. Chem. Chimica Therapeutica, 1977, vol. 12, pp. 231-235.

Known methods, such as described in March's Advanced Organic Chemistry, 5th Edition, 2005, ISBN 0471585890, are used to convert the R5 and/or R4 group of the compounds of formula (IV) according to the R5 and/or R4 substituents desired for the compounds of formula (I). It is also possible to convert the R5 and/or R4 group of the compounds of formula (I) in order to obtain novel compounds of formula (I) carrying the desired R5 and/or R4 substituents.

Thus, the group R5=$CO_2Me$ makes it possible to prepare compounds of formula (IV) or (I) in which R5 represents a $CO_2H$, CN or $CH_2OH$ group and the group R5=—$(CH_2)_m$—$CO_2Me$ makes it possible to prepare compounds of formula (IV) or (I) in which R5 represents a —$(CH_2)_m$—$CO_2R6$, —$(CH_2)_m$—CONR6R7, —$(CH_2)_m$—CONHNR6R7, —$(CH_2)_m$—CONR7OR8, —$(CH_2)_n$—NR6R7, —$(CH_2)_n$—NR6COR7 or —$(CH_2)_n$—NR6COOR7 group by methods known to a person skilled in the art.

It is possible, starting from a compound of formula (IV) or (I) comprising a group R5=$(CH_2)_n$—OH, with n=1, 2 or 3, to prepare a compound of formula (IV) or (I) in which R5=mesyloxymethyl, by reaction with mesyl chloride, and then a compound of formula (IV) or (I) in which R5=—$(CH_2)_n$—NR6R7, by reaction with HNR6R7, R6 and R7 being as defined for the compounds of formula (I).

The compounds according to the invention are obtained in the racemic form; the optically pure isomers can subsequently be prepared by using resolution methods known to a person skilled in the art, such as crystallization by formation of salts with chiral agents. It is also possible to prepare compounds according to the invention in the optically pure form by using asymmetric or stereospecific synthesis methods or chromatographic techniques using a chiral phase. Furthermore, the products of the invention can be separated via the formation of diastereoisomers, their separation and then the decomposition of the pharmacologically useful diastereoisomer to give its enantiomerically pure active product. Enzymatic techniques can also be employed. Additional known separating techniques can be used. They include those disclosed in: Enantiomers, Racemates and Resolutions, John Wiley and Sons, New York (1981).

The compounds according to the invention can also be prepared in the form enriched in a stereoisomer from the preparation of the synthetic intermediates. Thus, the resolution of the enantiomers of the amines of formula (III) or of the nitro precursors (IV) can be carried out by one of the above-mentioned methods.

The following examples describe the preparation of some intermediates and of compounds in accordance with the invention. These examples are not limiting and serve only to illustrate the present invention.

In the examples, the following abbreviations are used:
M.p.=melting point
Boc: tert-butoxycarbonyl
BOP: (benzotriazol-1-yloxy)tris(dimethylamino)phosphonium hexafluorophosphate
THF: tetrahydrofuran
AT: ambient temperature
DCM: dichloromethane
MeOH: methanol
DCCI: dicyclohexylcarbodiimide
DIPEA: diisopropylethylamine
$KHSO_4/K_2SO_4$: 5% solution of $KHSO_4/K_2SO_4$
Z: benzyloxycarbonyl The proton nuclear magnetic resonance (NMR) spectra are recorded at 200 MHz or at 250 MHz in $d_6$-DMSO, unless otherwise indicated. The $d_6$-DMSO signal is at 2.5 ppm and acts as reference. The following abbreviations are used in interpreting the spectra: s: singlet, d: doublet, t: triplet, m: unresolved peak, mt: multiplet, bs: broad singlet, dd: double doublet, q: quartet, qt: quintet, bt: broad triplet.

M.p.=melting point (in degrees Celsius), as measured on a Büchi B545 device with a temperature gradient of 1° C. per minute.

$MH^+$=mass spectrum. The compounds are analyzed by coupled HPLC/UV/MS (liquid chromatography/UV detection/mass spectrometry). The device used, sold by Agilent, is composed of an HP1100 chromatograph equipped with an Agilent diode array detector and with an MSD Quad quadrupole mass spectrometer.

The analytical conditions are as follows:

| | |
|---|---|
| Column: | Symmetry C18 (50 × 2.1 mm; 3.5 μm) |
| Eluent A: | $H_2O$ + 0.005% TFA at pH 3.15 |
| Eluent B: | $CH_3CN$ + 0.005% TFA |
| Gradient: | Time (min)　　　　% B |
| | 0　　　　0 |
| | 10　　　　90 |
| | 15　　　　90 |
| | 16　　　　0 |
| | 20　　　　0 |
| Column temperature: | 30° C. |
| Flow rate: | 0.4 ml/min |
| Detection: | λ = 210 nm | rt = retention time.

EXAMPLE 1

(R/S)-2-[[2-(aminomethyl)-1,3-benzodioxol-5-yl]amino]-6-(2,6-dichlorophenyl)-8-methyl-8H-pyrido[2,3-d]pyrimidin-7-one Stage 1: A mixture of 0.384 g of compound of formula (II), 6-(2,6-dichlorophenyl)-8-methyl-2-methylsulfonyl-8H-pyrido[2,3-d]pyrimidin-7-one, and 0.266 g of compound of formula (III), (R/S)-2-(N-Boc-aminomethyl)-1,3-benzodioxol-5-ylamine, is heated in 4 ml of acetic acid at 80° C. for 2 h. The reaction medium is subsequently concentrated by half under vacuum, then taken up in water and ethyl acetate and brought to pH 6 with a saturated $NaHCO_3$ solution; the organic phase is separated by settling, washed with water and then a saturated NaCl solution, dried over sodium sulfate and evaporated. The crude product obtained is purified by flash chromatography on silica with a gradient of 0 to 1% of methanol in dichloromethane. 0.252 g of expected product is obtained in the form of a yellow powder.

NMR: (DMSO, 200 MHz) 1.35 ppm: s: 9H, 3.25-3.40 ppm: mt: 2H, 3.60 ppm: s: 3H, 6.15 ppm: t: 1H, 6.85 ppm: d: 1H, 7.15 ppm: bd: 2H, 7.40-7.60 ppm: m: 4H, 7.85 ppm: s: 1H, 8.75 ppm: s: 1H, 10.10 ppm: s: 1H.

Stage 2: The amine functional group of $Ar_1$ is deprotected by treating 0.240 g of the preceding product in a mixture of 3.5 ml of dichloromethane and 3.5 ml of trifluoroacetic acid for 1 h. After concentrating to dryness under vacuum, the residue is taken up in a mixture of water and dichloromethane and the pH is brought to 9 with a 15% $Na_2CO_3$ solution; the organic phase is separated by settling, washed with water and then a saturated NaCl solution, dried over $Na_2SO_4$ and then evaporated; the yellow solid residue is triturated from ether, filtered off and then dried. w=0.121 g, $MH^+$: 470.

NMR: (DMSO, 200 MHz) 3.05 ppm: d: 2H, 3.60 ppm: s: 3H, 4.15 ppm: bs: 2H, 6.20 ppm: t: 1H, 6.85 ppm: d: 1H, 7.20 ppm: d: 1H, 7.35-7.65 ppm: m: 4H, 7.90 ppm: s: 1H, 8.80 ppm: s: 1H, 10.10 ppm: s: 1H.

Preparation of the Compound of Formula (III): (R/S)-2-(N-Boc-aminomethyl)-1,3-benzodioxol-5-ylamine Stage 1: 31.0 g of 4-nitrocatechol are added over 1 hour to 17.6 g of 60% NaH in suspension in 300 ml of DMF while cooling in order to keep the temperature below 30° C. The mixture is stirred for a further 15 minutes, 104 ml of methyl dichloroacetate are then added over 1 hour and then the mixture is stirred at 90° C. for 4 hours. The reaction medium is poured onto a mixture of 2 liters of ice/water and then extraction is carried out with 4 times 400 ml of AcOEt. The combined organic phases are washed once with a saturated NaCl solution, then dried and concentrated under vacuum (evaporation of DMF). The residue is taken up in an $AcOEt/H_2O$ mixture and the pH is brought to 8.6 with $Na_2CO_3$. The organic phase is separated by settling, washed with saturated $NaHCO_3$, $H_2O$, 5% $KHSO_4/K_2SO_4$, $H_2O$ and saturated NaCl and then dried and evaporated under vacuum. A semisolid residue is obtained and is taken up and then triturated from heptane to give a solid, w=27.7 g, M.p.=90-92° C.

Stage 2: 22.3 ml of a 1M $LiAlH_4$ solution in THF are added at -5° C. over 1 hour 15 minutes to 5.02 g of the methyl ester, obtained in the preceding preparation, dissolved in 25 ml of THF. 20 minutes after the end of the addition, 20 ml of AcOEt are added dropwise, followed by 9 ml of 1N NaOH. The precipitate formed is removed by filtration and washed with AcOEt. The filtrate is diluted with AcOEt and washed with $H_2O$, 5% $KHSO_4/K_2SO_4$, $H_2O$ and saturated NaCl. After drying and concentrating under vacuum, a wax is obtained, which wax crystallizes: w=2.74 g, M.p.=80-82° C.

Stage 3: 3 ml of triethylamine are added at 5° C. to 4.12 g of the alcohol, obtained in the preceding preparation, dissolved in 30 ml of $CH_2Cl_2$, followed in 15 minutes by 1.85 g of mesyl chloride. After 15 minutes, the ice bath is removed. After 55 minutes, the reaction medium is diluted with $CH_2Cl_2$ and water. The organic phase is separated by settling, washed with $H_2O$ and saturated NaCl, dried and evaporated. After triturating from heptane, the expected product is obtained, w=5.20 g, M.p.=112-115° C.

Stage 4: 1.51 g of sodium azide are added to 2.14 g of the mesylate, obtained in the preceding stage, dissolved in 17 ml of DMF, and the mixture is heated at 70° C. for 3 hours. The reaction medium is extracted with AcOEt, which is washed with water and then with a saturated NaCl solution. An oil is obtained.

w=1.71 g.

Stage 5: 3.41 g of triphenylphosphine are added portionwise to 1.7 g of the product, obtained in the preceding stage, dissolved in 20 ml of AcOEt, followed, after 10 minutes, by 2.34 ml of water, and the mixture is heated to 60° C. After 1 hour, the reaction medium is evaporated to dryness and the residue is then taken up in $Et_2O$. The insoluble materials are removed and then an excess of a saturated solution of HCl in ether is added. The solid formed is filtered off, washed with ether and then dried, in order for the expected product to be obtained in the hydrochloride form. The corresponding amine is obtained by release from the hydrochloride.

Stage 6: 1.49 ml of triethylamine and then, portionwise, 2.53 g of $Boc_2O$ are added to the product, obtained in the preceding stage, in 30 ml of DCM. After 1 hour, the reaction medium is washed with 5% $KHSO_4/K_2SO_4$, $H_2O$ and saturated NaCl. After drying, the organic phase is concentrated to dryness and then the residue is triturated from heptane. 2 g of the expected product are obtained in the solid form.

Stage 7: The product of formula (III) is obtained from 0.52 g of its nitro precursor of formula (IV) dissolved in 15 ml of THF. 1.72 g of powdered zinc are added and then, at -5° C., 2 ml of acetic acid are added in 30 min. Stirring is continued at ambient temperature for 3 h, the reaction medium is then filtered and the solid is rinsed with a small amount of THF in methanol. The filtrate is taken up in a mixture of water and ethyl acetate and brought to pH 9 with a 15% $Na_2CO_3$ solution. After separating by settling, the organic phase is washed with a saturated $NaHCO_3$ solution, then with water and then with a saturated NaCl solution. After drying over $Na_2SO_4$, the solvent is evaporated. A thick oil is obtained: yield of 100%.

NMR: (DMSO, 200 MHz) 1.35 ppm: s: 9H, 3.20-3.35 ppm: mt: 2H, 4.70 ppm: s: 2H, 5.85-6.05 ppm: m: 2H, 6.15 ppm: d: 1H, 6.50 ppm: d: 1H, 7.10 ppm: t: 1H.

EXAMPLE 2

6-(2,6-dichlorophenyl)-2-[(1,3-dihydro-5-iso-benzofuranyl)amino]-8-methyl-8H-pyrido[2,3-d]pyrimidin-7-one A mixture of 0.614 g of compound of formula (II), 6-(2,6-dichlorophenyl)-8-methyl-2-methylsulfonyl-8H-pyrido[2,3-d]pyrimidin-7-one, and 0.389 g of the compound of formula (III), (1,3-dihydro-5-isobenzofuranyl)amine, is heated in 10 ml of acetic acid at reflux for 20 min; the reaction medium is concentrated by half under vacuum, then taken up in a mixture of ethyl acetate and water and brought to pH 9 with a saturated $NaHCO_3$ solution. After separating by settling, the organic phase is washed with water and then with a saturated NaCl solution, dried over sodium sulfate and then evaporated to dryness. The product is purified by flash chromatography on silica with a gradient of 0 to 50% of ethyl acetate in dichloromethane. 0.140 g of expected product is obtained in the form of a yellow solid.

$MH^+$=439. NMR: (DMSO, 200 MHz) 3.65 ppm: s: 3H, 5.00 ppm: d: 4H, 7.25 ppm: d: 1H, 7.35-7.70 ppm: m: 5H, 7.90 ppm: s: 1H, 8.80 ppm: s: 1H, 10.25 ppm: s: 1H.

The preparation of the compound of formula (III) is described in J. Med. Chem., 1978, 21, pages 965-978.

EXAMPLE 3

2-(2,1,3-benzothiadiazol-5-ylamino)-6-(2,6-dichlorophenyl)-8-methyl-8H-pyrido[2,3-d]pyrimidin-7-one 184 mg of potassium tert-butoxide are added in three installments, at ambient temperature under argon, to 300 mg of compound of formula (II), 6-(2,6-dichlorophenyl)-8-methyl-2-methylsulfonyl-8H-pyrido[2,3-d]pyrimidin-7-one, and 170 mg of the compound of formula (III), 2,1,3-benzothiadiazol-5-ylamine, in suspension in 5 ml of DMSO. After a contact time of 30 minutes, the reaction medium is diluted with a mixture of water and ethyl acetate. The aqueous phase is extracted with ethyl acetate and the combined organic phases are then washed with water and then with a saturated NaCl solution. After drying over $Na_2SO_4$ and filtering, the solvent is evaporated and then the residue is taken up in a few milliliters of ethyl acetate. The green precipitate obtained is filtered off and then chromatographed on silica (gradient: DCM 100 to DCM/MeOH 90:10). 105 mg of the expected product are isolated in the solid form.

$MH^+$=455 NMR (DMSO, 200 MHz): 3.80 ppm: s: 3H, 7.45 ppm: dd: 1H, 7.65 ppm: d: 2H, 7.90-8.15 ppm: mt: 3H, 8.85 ppm: s: 1H, 9.00 ppm: s: 1H, 10.80 ppm: s: 1H.

The compound of formula (III) is commercially available.

EXAMPLE 4

6-(2,6-dichlorophenyl)-2-[(2,3-dihydro-6-benzofuranyl)amino]-8-methyl-8H-pyrido[2,3-d]pyrimidin-7-one 1 g of compound of formula (II), 6-(2,6-dichlorophenyl)-8-methyl-2-methylsulfonyl-8H-pyrido[2,3-d]pyrimidin-7-one, and 352 mg of the compound of formula (III), (2,3-dihydro-6-benzofuranyl)amine, are heated at 80° C. in 10 ml of acetic acid for 1 h 30. After returning to ambient temperature, the medium is filtered in order to remove an impurity, diluted with water and ethyl acetate and brought to pH 9 with $NaHCO_3$. The organic phase is then washed with a saturated NaCl solution, dried over $Na_2SO_4$ and concentrated under vacuum. The residue is chromatographed on silica (gradient: heptane 100 to heptane/ethyl acetate 40:60) to give 201 mg of the expected product in the form of a yellow solid.

$MH^+$=439 NMR (DMSO, 250 MHz): 3.15 ppm: t: 2H, 3.65 ppm: s: 3H, 4.55 ppm: t: 2H, 7.10-7.25 ppm: mt: 2H, 7.40-7.50 ppm: mt: 2H, 7.55 ppm: d: 2H, 7.90 ppm: s: 1H, 8.85 ppm: s: 1H, 10.20 ppm: s: 1H.

The preparation of the compound of formula (III) is described in Eur. J. Med. Chem. Chimica Therapeutica, 1977, vol. 12, pp. 231-235.

EXAMPLE 5

(2R)-2-amino-3-[4-[[6-(2,6-dichlorophenyl)-7,8-dihydro-8-methyl-7-oxopyrido[2,3-d]pyrimidin-2-yl]-amino]phenoxy]-N,N-dimethylpropanamide Stage 1: A suspension of 4.23 g of the compound of formula (III), methyl (2R)-3-(para-aminophenyloxy)-2-(N-Boc-amino)propanoate, and 4.10 g of compound of formula (II), 6-(2,6-dichlorophenyl)-8-methyl-2-methylsulfonyl-8H-pyrido[2,3-d]pyrimidin-7-one, in 40 ml of acetic acid is heated at 90° C. for 1.5 hours. After returning to ambient temperature, the reaction medium is concentrated under vacuum and chromatographed on silica (gradient: heptane 100 to heptane/ethyl acetate 35:65) to give 2.39 g of the expected product in the form of a yellow solid.

$^1$H NMR (DMSO, 200 MHz): 1.40 ppm: s: 9H, 3.60 ppm: s: 3H, 3.65 ppm: s: 3H, 4.15-4.25 ppm: mt: 2H, 4.35-4.50: mt: 1H, 6.95 ppm: d: 2H, 7.35-7.50 ppm: mt: 2H, 7.55-7.60 ppm: mt: 2H, 7.75 ppm: d: 2H, 7.85 ppm: s: 1H, 8.80 ppm: s: 1H, 10.05 ppm: bs: 1H.

Stage 2: 117 mg of LiOH are added, at 0° C., to 1.50 g of the product obtained above in solution in 16 ml of tetrahydrofuran and 4 ml of water. After a contact time of 2 hours at 0° C., the reaction is terminated. The reaction medium is then hydrolyzed with water, diluted with ethyl acetate and acidified down to pH 1 with 2N HCl. The organic phase is washed with water and with a saturated NaCl solution, dried over sodium sulfate and concentrated under vacuum. The residue is chromatographed on silica (gradient: dichloromethane 100 to dichloromethane/methanol 80:20) to give 1.01 g of the expected product in the form of a yellow solid.

$^1$H NMR (DMSO, 200 MHz): 1.35 ppm: s: 9H, 3.60 ppm: s: 3H, 4.00-4.10 ppm: mt: 1H, 4.15-4.25: mt: 2H, 6.55 ppm: bs: 1H, 6.95 ppm: d: 2H, 7.45 ppm: dd: 1H, 7.55-7.65 ppm: mt: 2H, 7.70 ppm: d: 2H, 7.85 ppm: s: 1H, 8.80 ppm: s: 1H, 10.05 ppm: bs: 1H.

Stage 3: 136 mg of dimethylamine hydrochloride, 729 mg of (benzotriazol-1-yloxy)tris(dimethylamino)phosphonium hexafluorophosphate and 1.12 ml of diisopropylethylamine are successively added, at ambient temperature under nitrogen, to 900 mg of the product obtained above in solution in 20 ml of dimethylformamide. After a contact time of 1 hour, the reaction is terminated. The reaction medium is then hydrolyzed with water and diluted with ethyl acetate. The organic phase is washed with water and with a saturated NaCl solution, dried over sodium sulfate and concentrated under vacuum. The residue is chromatographed on silica (gradient: heptane/ethyl acetate 80:20 to heptane/ethyl acetate 20:80) to give 898 mg of the expected product in the form of a yellow solid.

$^1$H NMR (DMSO, 200 MHz): 1.35 ppm: s: 9H, 2.85 ppm: s: 3H, 3.05 ppm: s: 3H, 3.65 ppm: s: 3H, 3.95-4.15 ppm: mt: 2H, 4.70-4.80 ppm: mt: 1H, 6.90 ppm: d: 2H, 7.25 ppm: d: 1H, 7.45 ppm: dd: 1H, 7.55-7.65 ppm: mt: 2H, 7.70 ppm: d: 2H, 7.85 ppm: s: 1H, 8.80 ppm: s: 1H, 10.05 ppm: bs: 1H.

Stage 4: 10 ml of trifluoroacetic acid are added, at ambient temperature, to 800 mg of the product obtained above in solution in 10 ml of dichloromethane. After a contact time of 15 minutes, the reaction is terminated and the reaction medium is concentrated under vacuum. The residue is taken up in a mixture of water and dichloromethane and then brought to pH 9 by addition of $NaHCO_3$. The organic phase is then washed with water and with a saturated NaCl solution, dried over sodium sulfate and concentrated under vacuum. After taking the residue up in diethyl ether and filtering, 545 mg of the expected product are isolated in the form of a yellow solid.

$MH^+$=527 $^1$H NMR (DMSO, 250 MHz): 1.80 ppm: bs: 2H, 2.85 ppm: s: 3H, 3.05 ppm: s: 3H, 3.60 ppm: s: 3H, 3.85 ppm: dd: 1H, 3.90-4.10 ppm: mt: 2H, 6.95 ppm: d: 2H, 7.45 ppm: dd: 1H, 7.60 ppm: d: 2H, 7.75 ppm: d: 2H, 7.85 ppm: s: 1H, 8.80 ppm: s: 1H, 10.05 ppm: bs: 1H.

Enantiomeric purity (technique: Chiral SFC; detection U.V. 210 nm; column Chiralpak AS-H, 250×4.6 mm, 5 µm; mobile phase: 80/20 $(CO_2)$/(ethanol+0.5% isopropanol); flow rate 2.4 ml/min; pressure: 200 bar; temperature: 30° C.): 1.9% enantiomer 1 (S) 98.1% enantiomer 2 (R)

Preparation of the Compound of Formula (III): methyl (2R)-3-(para-aminophenyloxy)-2-(N-Boc-amino)propanoate Stage 1: 36.82 ml of triethylamine are added, at ambient temperature under nitrogen, to 20.00 g of the methyl ester derivative of (D)-serine in solution in 250 ml of dichloromethane. After cooling the reaction medium to 0° C., a solution of trityl chloride in 200 ml of dichloromethane is run in so as to maintain the temperature of the medium between 0° C. and 5° C. After a contact time of 3 hours at 5° C., the reaction medium is washed with a saturated $NH_4Cl$ solution, with water and with a saturated NaCl solution, dried over sodium sulfate and concentrated under vacuum. The residue is taken up in diethyl ether. The precipitate obtained is filtered off and 41.72 g of the expected product are isolated after drying in the form of a white solid.

¹H NMR (DMSO, 200 MHz): 2.80 ppm: d: 1H, 3.15-3.25 ppm: mt: 1H, 3.30 ppm: s: 3H, 3.35-3.50 ppm: mt: 1H, 3.55-3.70 ppm: mt: 1H, 4.90 ppm: t: 1H, 7.10-7.50 ppm: mt: 15H.

Stage 2: 37.19 g of triphenylphosphine, 20.13 g of p-nitrophenol and 23.02 ml of diethyl azodicarboxylate are successively added, at ambient temperature under nitrogen, to 41.00 g of the product obtained above in solution in 1250 ml of tetrahydrofuran. After a contact time of 20 minutes, the reaction medium is diluted with ethyl acetate. The organic phase is washed with a saturated NaHCO₃ solution and with a saturated NaCl solution, dried over sodium sulfate and concentrated under vacuum. The residue is chromatographed on silica (gradient: heptane 100 to heptane/ethyl acetate 70:30) to give 36.12 g of the expected product in the form of a white solid.

¹H NMR (CDCl₃, 200 MHz): 2.90 ppm: d: 1H, 3.25 ppm: s: 3H, 3.70-3.80 ppm: mt: 1H, 4.05 ppm: dd: 1H, 4.30 ppm: dd: 1H, 6.90 ppm: d: 2H, 7.10-7.35 ppm: mt: 9H, 7.55 ppm: d: 6H, 8.15 ppm: d: 2H.

Stage 3: 360 ml of trifluoroacetic acid are added, at ambient temperature, to 36.00 g of the product obtained above in solution in 370 ml of dichloromethane. After a contact time of 30 minutes, the reaction is terminated and the reaction medium is concentrated under vacuum. The residue is taken up in diethyl ether, the precipitate is then filtered off and 12.027 g of the expected product (product in the form of the trifluoroacetic acid salt) are isolated after drying.

¹H NMR (DMSO, 200 MHz): 3.80 ppm: s: 3H, 4.45 ppm: dd: 1H, 4.60 ppm: dd: 1H, 4.65-4.80 ppm: mt: 1H, 7.20 ppm: d: 2H, 8.25 ppm: d: 2H, 8.75 ppm: bs: 3H.

Stage 4: 20.54 ml of triethylamine and 13.26 g of di(tert-butyl) dicarbonate are successively added, at ambient temperature under nitrogen, to 11.80 g of the product obtained above, in the form of the TFA salt, in solution in 200 ml of dichloromethane. After a contact time of 4 hours, the reaction medium is hydrolyzed with a 5% aqueous KHSO₄/K₂SO₄ solution. The organic phase is washed with water and with a saturated NaCl solution, dried over sodium sulfate and concentrated under vacuum. The residue is chromatographed on silica (gradient: heptane 100 to heptane/ethyl acetate 50:50) and 10.41 g of the expected product are obtained in the form of a yellow solid.

¹H NMR (DMSO, 200 MHz): 1.40 ppm: s: 9H, 3.65 ppm: s: 3H, 4.35 ppm: d: 2H, 4.45-4.55 ppm: mt: 1H, 7.15 ppm: d: 2H, 7.55 ppm: d: 1H, 8.20 ppm: d: 2H.

Stage 5: 30.70 ml of acetic acid are run into a solution of 10.15 g of the nitro product obtained above and 29.25 g of zinc in 300 ml of tetrahydrofuran while maintaining the temperature between 0° C. and −5° C. After returning to ambient temperature and a contact time of 3 hours, the reaction medium is diluted with ethyl acetate and filtered through celite. The organic phase is basified by addition of NaHCO₃ and then washed with a saturated NaHCO₃ solution and with a saturated NaCl solution. After drying over sodium sulfate and concentrating under vacuum, 9.41 g of an orange oil are isolated. A compound of formula (III), where Ar'₁ is a precursor of Ar₁ which will be modified after the addition reaction with a compound of formula (II), is obtained.

¹H NMR (DMSO, 200 MHz): 1.40 ppm: s: 9H, 3.65 ppm: s: 3H, 4.05 ppm: d: 2H, 4.25-4.45 ppm: mt: 1H, 4.65 ppm: bs: 2H, 6.45 ppm: d: 2H, 6.65 ppm: d: 2H, 7.35 ppm: d: 1H.

EXAMPLE 6

(2S)-2-amino-3-[4-[[6-(2,6-dichlorophenyl)-7,8-dihydro-8-methyl-7-oxopyrido[2,3-d]pyrimidin-2-yl]-amino]phenoxy]-N,N-dimethylpropanamide The product of example 6 is synthesized in the same way as that of example 5, (D)-serine being replaced with (L)-serine.

MH⁺=527 Enantiomeric purity (identical analytical conditions to those of example 5): 99.6% enantiomer 1 (S) 0.4% enantiomer 2 (R)

EXAMPLE 7

2-(2,1,3-benzothiadiazol-5-ylamino)-8-cyclopentyl-6-(2,6-dichlorophenyl)-8H-pyrido[2,3-d]pyrimidin-7-one 202 mg of potassium tert-butoxide are added in 3 installments, at ambient temperature under argon, to 500 mg of compound of formula (II), 8-cyclopentyl-6-(2,6-dichlorophenyl)-2-methylsulfonyl-8H-pyrido[2,3-d]pyrimidin-7-one, and 249 mg of the compound of formula (III), 2,1,3-benzothiadiazol-5-ylamine, in suspension in 18 ml of DMSO. After a contact time of 45 min, the reaction medium is diluted with a mixture of water and ethyl acetate. The aqueous phase is extracted with ethyl acetate and the combined organic phases are then washed with water and then with a saturated NaCl solution. After drying over sodium sulfate and filtering, the residue is chromatographed on silica (gradient: heptane 100 to heptane/ethyl acetate 60:40) and precipitated from diethyl ether to give 283 mg of the expected product in the form of a yellow solid.

MH⁺=509 ¹H NMR (400 MHz, DMSO): 1.60-1.80 ppm: mt: 2H, 1.85-2.05 ppm: mt: 4H, 2.20-2.40 ppm: mt: 2H, 5.95-6.10 ppm: mt: 1H, 7.45-7.55 ppm: mt: 1H, 7.60-7.70 ppm: mt: 2H, 7.95-8.15 ppm: mt: 3H, 8.75 ppm: s: 1H, 9.0 ppm: s: 1H, 10.70 ppm: s: 1H.

The compound of formula (III) is commercially available.

The preparation of the compound of formula (II) is described in J. Med. Chem., 1998, 41, 3276-3292, from cyclopentylamine and ethyl 4-chloro-2-(methylsulfanyl)pyrimidine-5-carboxylate.

EXAMPLE 8

(R/S)-N-methylamide of 7-[6-(2,6-dichlorophenyl)-8-methyl-7-oxo-7,8-dihydropyrido[2,3-d]pyrimidin-2-ylamino]-2,3-dihydrobenzo[1,4]dioxin-2-carboxylic acid 600 mg of compound of formula (III), described below, and 1.11 g of compound of formula (II), 6-(2,6-dichlorophenyl)-8-methyl-2-methylsulfonyl-8H-pyrido[2,3-d]pyrimidin-7-one, are dissolved in 10 ml of THF. The reaction medium is heated at 110° C. in a sealed tube for 24 h. After concentrating to dryness, the residue is chromatographed on silica (gradient: heptane 100 to heptane/ethyl acetate 10:90) and 661 mg of the expected product are isolated in the form of a yellow solid.

MH⁺=512 ¹H NMR (400 MHz, DMSO): 2.65 ppm: bs: 3H, 3.65 ppm: s: 3H, 4.15-4.25 ppm: mt: 1H, 4.30-4.40 ppm: mt: 1H, 4.75-4.80 ppm: mt: 1H, 6.85 ppm: d: 1H, 7.30 ppm: bd: 1H, 7.40-7.50 ppm: mt: 1H, 7.55-7.65 ppm: mt: 3H, 7.80 ppm: s: 1H, 8.10 ppm: bs: 1H, 8.80 ppm: s: 1H, 10.05 ppm: bs: 1H.

Preparation of the Compound of Formula (III):
(R/S)-N-methylamide of 7-amino-2,3-dihydrobenzo
[1,4]dioxin-2-carboxylic acid Stage 1: 2.44 ml of 2M methylamine in THF, 0.85 ml of DIPEA and 1.57 g of TBTU are added to a solution of 1 g of 7-nitro-2,3-dihydrobenzo[1,4]dioxin-2-carboxylic acid in the racemic form (described in the publication Journal of Organic Chemistry, 46, 19, 3846-3852) in 10 ml of THF. After a contact time of 4 h at ambient temperature, the reaction medium is concentrated to dryness and the residue taken up in ethyl acetate. The organic phase is washed with a saturated $Na_2CO_3$ solution, with a 5% $KHSO_4/K_2SO_4$ solution, with water and finally with a saturated NaCl solution. After drying over sodium sulfate and concentrating, 900 mg of the expected product are isolated in the form of a yellow solid.

$MH^+$=239 $^1$H NMR (200 MHz, DMSO): 2.60 ppm: d: 3H, 4.45 ppm: d: 2H, 4.95 ppm: t: 1H, 7.10 ppm: d: 1H, 7.70-7.85 ppm: mt: 2H, 8.20 ppm: bs: 1H.

Stage 2: 3.90 ml of acetic acid are run onto a solution of 900 mg of the amide obtained above and 3.71 g of zinc in 15 ml of THF while maintaining the temperature between 0° C. and −5° C. After returning to ambient temperature, the reaction medium is diluted with ethyl acetate and filtered through celite. The organic phase is basified by addition of $NaHCO_3$ and then washed with water and with a saturated NaCl solution. After drying over sodium sulfate and concentrating under vacuum, 700 mg of the expected compound of formula (III) are isolated.

$MH^+$=209 $^1$H NMR (200 MHz, DMSO): 2.60 ppm: d: 3H, 4.05-4.20 ppm: mt: 2H, 4.65 ppm: dd: 1H, 4.70 ppm: bs: 2H, 6.10 ppm: dd: 1H, 6.20 ppm: d: 1H, 6.55 ppm: d: 1H, 8.00 ppm: bs: 1H.

EXAMPLE 9

(R/S)-2-(2-aminomethyl-2,3-dihydrobenzo[1,4]dioxin-6-ylamino)-6-(2,6-dichlorophenyl)-8-methyl-8H-pyrido[2,3-d]pyrimidin-7-one Stage 1: 558 mg of compound of formula (II), 6-(2,6-dichlorophenyl)-8-methyl-2-methylsulfonyl-8H-pyrido[2,3-d]pyrimidin-7-one, and 407 mg of compound of formula (III), described below, dissolved in 5 ml of THF, are heated at 110° C. in a sealed tube in a microwave oven for 45 min. After concentrating to dryness, the residue is chromatographed on silica (gradient: heptane 100 to heptane/EtOAc 30:70) to give 400 mg of the expected product in the solid form.

$^1$H NMR (200 MHz, DMSO): 1.40 ppm: s: 9H, 3.15-3.30 ppm: mt: 2H 3.65 ppm: s: 3H, 3.85-4.00 ppm: mt: 1H, 4.10-4.20 ppm: mt: 1H, 4.25-4.35 ppm: mt: 1H, 6.85 ppm: d: 1H, 7.10 ppm: bt: 1H, 7.25 ppm: dd: 1H, 7.40-7.65 ppm: mt: 4H, 7.90 ppm: s: 1H, 8.80 ppm: s: 1H, 10.05 ppm: bs: 1H.

Stage 2: 4.3 ml of TFA are added at ambient temperature to 400 mg of N-Boc intermediate dissolved in 4 ml of $CH_2Cl_2$. After a contact time of 1 h 30 min, the reaction medium is concentrated to dryness and the residue is then taken up in a mixture of water and ethyl acetate and basified up to a pH of 10 with $Na_2CO_3$. The aqueous phase is extracted with ethyl acetate. The combined organic phases are washed with a saturated NaCl solution, dried over sodium sulfate and concentrated to dryness. The residue is chromatographed on silica (gradient: $CH_2Cl_2$ 100 to $CH_2Cl_2$/MeOH 80:20) to give 133 mg of the expected product in the racemic form.

$MH^+$=484 $^1$H NMR (400 MHz, DMSO): 2.70-2.90 ppm: mt: 2H, 3.65 ppm: s: 3H, 3.95-4.05 ppm: mt: 1H, 4.10-4.20 ppm: mt: 1H, 4.40 ppm: d: 1H, 6.85 ppm: d: 1H, 7.25 ppm: d: 1H, 7.40-7.55 ppm: mt: 2H, 7.60-7.65 ppm: mt: 2H, 7.90 ppm: s: 1H, 8.80 ppm: s: 1H, 10.05 ppm: bs: 1H.

Preparation of the Compound of Formula (III):
(R/S)-2-(N-Boc-aminomethyl)-2,3-dihydrobenzo[1,4]dioxin-6-ylamine Stage 1: 1.350 g of sodium azide are added, under nitrogen, to a solution of 2 g of the (6-nitro-2,3-dihydrobenzo[1,4]dioxin-2-yl)methyl ester of methanesulfonic acid in the racemic form (described in patent application WO 01/021577) in 14 ml of DMF. After a contact time of 6 h at 65° C. and leaving overnight at ambient temperature, the reaction medium is hydrolyzed on a water/ice mixture and extracted with ethyl acetate. The organic phase is washed with a saturated NaCl solution, dried over sodium sulfate and concentrated to give 1.60 g of the expected product.

$^1$H NMR (200 MHz, DMSO): 3.65-3.75 ppm: mt: 2H, 4.15 ppm: dd: 1H, 4.45 ppm: dd: 1H, 4.55-4.70 ppm: mt: 1H, 7.15 ppm: d: 1H, 7.70-7.85 ppm: mt: 2H.

Stage 2: 1.5 g of the azide obtained above are dissolved in 40 ml of ethyl acetate and 2 ml of water. After adding 2.83 g of triphenylphosphine, the reaction medium is heated at 60° C. for 2 h and then concentrated to dryness. The residue is taken up in toluene and reevaporated twice in succession. After adding diethyl ether and filtering off an insoluble material, the organic phase is acidified with ethereal hydrochloric acid. The precipitate formed is filtered off, washed with diethyl ether and dried to give 1.59 g of the expected product in the form of the hydrochloride.

$^1$H NMR (200 MHz, DMSO): 3.00-3.25 ppm: mt: 2H, 4.20 ppm: dd: 1H, 4.50 ppm: dd: 1H, 4.55-4.70 ppm: mt: 1H, 7.15 ppm: d: 1H, 7.75-7.90 ppm: mt: 2H, 8.45 ppm: bs: 3H.

Stage 3: 1.80 ml of triethylamine and 1.83 g of di(tert-butyl) dicarbonate are added, at ambient temperature, to 1.59 g of the amine obtained above dissolved in 20 ml of dichloromethane. After 1 h at ambient temperature, the reaction medium is diluted with a dichloromethane/water mixture. The organic phase is washed with a 5% $KHSO_4/K_2SO_4$ solution and then with a saturated NaCl solution. After drying over sodium sulfate and concentrating, the residue is taken up in heptane. The precipitate formed is filtered off, washed with heptane and dried to give 1.45 g of the expected product.

$^1$H NMR (200 MHz, DMSO): 1.40 ppm: s: 9H, 3.00-3.25 ppm: mt: 2H, 4.05 ppm: dd: 1H, 4.25-4.45 ppm: mt: 2H, 7.10 ppm: d: 1H, 7.15 ppm: bt: 1H, 7.70-7.85 ppm: mt: 2H.

Stage 4: 4.81 ml of acetic acid are run onto a solution of 1.45 g of the carbamate obtained above and 4.58 g of zinc in 18 ml of tetrahydrofuran while maintaining the temperature between 0° C. and −5° C. After returning to ambient temperature, the reaction medium is diluted with ethyl acetate and filtered through celite. After addition of water, the organic phase is basified by addition of $NaHCO_3$ up to a pH of 8-9 and then washed with water and with a saturated NaCl solution. After drying over sodium sulfate and concentrating under vacuum, 1.15 g of the expected compound of formula (III) are isolated.

$^1$H NMR (200 MHz, DMSO): 1.40 ppm: s: 9H, 3.00-3.25 ppm: mt: 2H, 3.70-3.85 ppm: mt: 1H, 3.95-4.05 ppm: mt: 1H, 4.15 ppm: dd: 1H; 4.60 ppm: bs: 2H, 6.00-6.10 ppm: mt: 2H, 6.50 ppm: d: 1H, 7.05 ppm: bt: 1H.

EXAMPLE 10

(R/S)-N-ethylamide of 6-[6-(2,6-dichlorophenyl)-8-methyl-7-oxo-7,8-dihydropyrido[2,3-d]pyrimidin-2-ylamino]-2,3-dihydrobenzofuran-2-carboxylic acid 261 mg of compound of formula (II), 6-(2,6-dichlorophenyl)-8-methyl-2-methylsulfonyl-8H-pyrido[2,3-d]pyrimidin-7-one, and 140 mg of compound of formula (III), described below, dissolved in 2 ml of THF are heated at 110° C. in a sealed tube in a microwave oven for 3 h. After concentrating to dryness, the residue is chromatographed on silica (gradient: heptane 100 to heptane/EtOAc 30:70) to give 67 mg of the expected product in the solid form.

$MH^+$=510 $^1$H NMR (250 MHz, DMSO): 1.00 ppm: t: 3H, 3.00-3.20 ppm: mt: 2H, 3.40-3.45 ppm: mt: 2H, 3.60 ppm: s: 3H, 5.05 ppm: dd: 1H, 7.10 ppm: d: 1H, 7.25 ppm: d: 1H, 7.35-7.45 ppm: mt: 2H, 7.50-7.60 ppm: mt: 2H, 7.85 ppm: s: 1H, 8.10 ppm: bt: 1H, 8.80 ppm: s: 1H, 10.20 ppm: s: 1H.

Preparation of the Compound of Formula (III):
(R/S)-N-ethylamide of 6-amino-2,3-dihydrobenzofuran-2-carboxylic acid Stage 1: A suspension of 4.5 g of 2-hydroxy-4-nitrobenzaldehyde (described in patent application WO 2006007693), 6.76 g of diethyl bromomalonate and 3.72 g of $K_2CO_3$ in 40 ml of methyl ethyl ketone is heated at reflux for 9 h. After returning to ambient temperature and taking the residue up in a mixture of water and ethyl acetate, the medium is acidified down to pH 3. The aqueous phase is extracted with ethyl acetate. The combined organic phases are washed with a saturated NaCl solution, dried over sodium sulfate and concentrated to dryness. The residue is chromatographed on silica (gradient: heptane 100 to heptane/EtOAc 80:20) to give 3.75 g of the expected product.

$^1$H NMR (200 MHz, DMSO): 1.35 ppm: t: 3H, 4.40 ppm: q: 2H, 7.90 ppm: s: 1H, 8.05 ppm: d: 1H, 8.25 ppm: dd: 1H, 8.75 ppm: bs: 1H.

Stage 2: A suspension of 3.75 g of the benzofuran derivative obtained above and 3.39 g of 10% palladium-on-charcoal in 55 ml of methanol is heated at 45° C. under 10 bar of hydrogen for 48 h. After returning to ambient temperature, the reaction medium is filtered through celite and concentrated to dryness to give 3 g of the expected product, which is used without additional purification in the following stage.

Stage 3: 1 g of the intermediate obtained in the preceding stage, dissolved in 2.5 ml of 2M ethylamine in THF, is heated at 150° C. in a sealed tube in a microwave oven for 40 min. After concentrating to dryness, the residue is chromatographed on silica (gradient: heptane 100 to heptane/EtOAc 40:60) to give 200 mg of the expected compound of formula (III).

$MH^+$=207 $^1$H NMR (200 MHz, DMSO): 1.00 ppm: t: 3H, 2.90-3.30 ppm: mt: 4H, 4.90-5.05 ppm: mt: 3H, 6.00-6.10 ppm: mt: 2H, 6.80 ppm: d: 1H, 8.00 ppm: bt: 1H.

EXAMPLE 11

(R/S)-N-ethylamide of 5-[6-(2,6-dichlorophenyl)-8-methyl-7-oxo-7,8-dihydropyrido[2,3-d]pyrimidin-2-ylamino]-2,3-dihydrobenzofuran-2-carboxylic acid 1.06 g of compound of formula (II), 6-(2,6-dichlorophenyl)-8-methyl-2-methylsulfonyl-8H-pyrido[2,3-d]pyrimid-7-one, and 570 mg of compound of formula (III), described below, dissolved in 20 ml of THF are heated at 120° C. in a sealed tube for 72 h. After concentrating to dryness, the residue is chromatographed on silica (gradient: $CH_2Cl_2$ 100 to $CH_2Cl_2$/MeOH 80:20) to give 133 mg of the expected product.

$MH^+$=510 $^1$H NMR (250 MHz, DMSO): 0.90 ppm: t: 3H, 3.00-3.30 ppm: mt: 3H, 3.45-3.55 ppm: mt: 1H, 3.60 ppm: s: 3H, 5.05 ppm: dd: 1H, 6.80 ppm: d: 1H, 7.40-7.70 ppm: mt: 5H, 7.80 ppm: s: 1H, 8.10 ppm: bt: 1H, 8.75 ppm: s: 1H, 10.00 ppm: s: 1H.

Preparation of the Compound of Formula (III):
(R/S)-N-ethylamide of 5-amino-2,3-dihydrobenzofuran-2-carboxylic acid Stage 1: A suspension of 10 g of the methyl ester of 5-nitrobenzofuran-2-carboxylic acid and 6 g of 10% palladium-on-charcoal in 100 ml of methanol is stirred at 30° C. under 10 bar of hydrogen for 48 h. After returning to ambient temperature, the reaction medium is filtered through celite and concentrated to dryness. The residue is chromatographed on silica (gradient: heptane 100 to heptane/EtOAc 40:60) to give 5 g of the expected product in the racemic form.

$MH^+$=208

Stage 2: 1.08 g of the intermediate obtained in the preceding stage, dissolved in 2.5 ml of 2M ethylamine in THF, are heated at 150° C. in a sealed tube in a microwave oven for 40 min. After concentrating to dryness, the residue is chromatographed on silica (gradient: $CH_2Cl_2$ 100 to $CH_2Cl_2$/MeOH 95:5) to give 630 mg of the expected compound of formula (III) in the racemic form.

$MH^+$=207 $^1$H NMR (250 MHz, DMSO): 0.90 ppm: t: 3H, 2.90-3.30 ppm: mt: 4H, 4.55 ppm: bs: 2H, 4.90 ppm: dd: 1H, 6.30 ppm: dd: 1H, 6.40 ppm: bs: 1H, 6.50 ppm: d: 1H, 7.95 ppm: bt: 1H.

EXAMPLE 12

(R/S)-2-(2-aminomethyl-2,3-dihydrobenzofuran-5-ylamino)-6-(2,6-dichlorophenyl)-8-methyl-8H-pyrido[2,3-d]pyrimidin-7-one Stage 1: 503 mg of compound of formula (III), described below, and 731 mg of compound of formula (II), 6-(2,6-dichlorophenyl)-8-methyl-2-methylsulfonyl-8H-pyrido[2,3-d]pyrimidin-7-one, are dissolved in 30 ml of THF. The reaction medium is heated at 120° C. in a sealed tube for 24 h. After concentrating to dryness, the residue is chromatographed on silica (gradient: heptane 100 to heptane/ethyl acetate 50:50) to give 730 mg of the expected product.

$^1$H NMR (250 MHz, DMSO): 1.45 ppm: s: 9H, 2.80-2.95 ppm: mt: 1H, 3.10-3.25 ppm: mt: 3H, 3.60 ppm: s: 3H, 4.70-4.80 ppm: mt: 1H, 6.70 ppm: d: 1H, 7.05 ppm: t: 1H, 7.40-7.50 ppm: mt: 2H, 7.55-7.65 ppm: mt: 3H, 7.80 ppm: s: 1H, 8.75 ppm: s: 1H, 10.00 ppm: s: 1H.

Stage 2: 4 ml of TFA are added, at ambient temperature, to 730 mg of the N-Boc intermediate dissolved in 10 ml of $CH_2Cl_2$. After a contact time of 1 h, the reaction medium is diluted with a dichloromethane/water mixture and basified up to pH 9 with $NaHCO_3$. The organic phase is washed with water and with a saturated NaCl solution, dried over sodium sulfate and concentrated to dryness. The residue is chromatographed on silica (gradient: $CH_2Cl_2$ 100 to $CH_2Cl_2$/MeOH 90:10 and then to $CH_2Cl_2$/MeOH/$NH_4OH$ 90:10:0.01) to give 160 mg of the expected product in the solid form.

$MH^+$=468 $^1$H NMR (250 MHz, DMSO): 1.55 ppm: bs: 2H, 2.85-3.00 ppm: dd: 1H, 3.10-3.25 ppm: mt: 3H, 3.60 ppm: s:

3H, 4.70-4.80 ppm: mt: 1H, 6.65 ppm: d: 1H, 7.40-7.50 ppm: mt: 2H, 7.55-7.65 ppm: mt: 3H, 7.80 ppm: s: 1H, 8.75 ppm: s: 1H, 10.00 ppm: s: 1H.

Preparation of the Compound of Formula (III): (R/S)-2-(N-Boc-aminomethyl)-2,3-dihydrobenzofuran-5-ylamine Stage 1: A solution composed of 2 g of ethyl (R/S)-5-amino-2,3-dihydrobenzofuran-2-carboxylate, obtained in stage 1 of the preparation of the compound of formula (III) of example 11, and 30 ml of ethanol is saturated with ammonia and then heated at 60° C. in a sealed tube for 12 h. After evaporating to dryness, 2 g of the expected intermediate are isolated.

MH$^+$=179 $^1$H NMR (250 MHz, DMSO): 3.05 ppm: dd: 1H, 3.25 ppm: dd: 1H, 4.5 ppm: bs: 2H, 4.85 ppm: dd: 1H, 6.30 ppm: dd: 1H, 6.40 ppm: bs: 1H, 6.45 ppm: d: 1H, 7.25 ppm: bs: 1H, 7.35 ppm: bs: 1H.

Stage 2: 2 g of the amide obtained above, in solution in 60 ml of THF, are added to 852 mg of LiAlH$_4$ in suspension in 60 ml of THF under nitrogen. After refluxing for 8 h and returning to ambient temperature overnight, the reaction medium is cooled in an ice bath and 0.85 ml of water, then 0.85 ml of a 5N sodium hydroxide solution and finally 2.55 ml of water are added. Stirring is maintained for 1 h and then the medium is filtered through celite and concentrated to dryness to generate 1.55 g of the expected product.

MH$^+$=165

Stage 3: 1.31 ml of triethylamine and 1.03 g of di(tert-butyl) dicarbonate are added, at ambient temperature, to 1.55 g of the preceding amine dissolved in 10 ml of dichloromethane. After 1 h at ambient temperature, the reaction medium is diluted with a dichloromethane/water mixture. The organic phase is washed with a 5% KHSO$_4$/K$_2$SO$_4$ solution and then with a saturated NaCl solution. After drying over sodium sulfate and concentrating, the residue is chromatographed on silica (gradient: heptane 100 to heptane/ethyl acetate 30:70) to give 1 g of the expected compound of formula (III).

$^1$H NMR (250 MHz, DMSO): 1.35 ppm: s: 9H, 2.60-2.80 ppm: mt: 1H, 2.95-3.15 ppm: mt: 3H, 4.45 ppm: bs: 2H, 4.50-4.65 ppm: mt: 1H, 6.25 ppm: dd: 1H, 6.30-6.45 ppm: mt: 2H, 6.95 ppm: t: 1H.

EXAMPLE 13

2-(2,1,3-benzothiadiazol-5-ylamino)-6-(2,6-dichlorophenyl)-8-prop-2-ynyl-8H-pyrido[2,3-d]pyrimidin-7-one Stage 1: 62 mg of potassium tert-butoxide are added in 3 installments, at ambient temperature under argon, to 180 mg of compound of formula (II), described below, 8-[3-((tert-butyl)dimethylsilanyl)prop-2-ynyl]-6-(2,6-dichlorophenyl)-2-methylsulfonyl-8H-pyrido[2,3-d]pyrimidin-7-one, and 81 mg of the compound of formula (III), 2,1,3-benzothiadiazol-5-ylamine, in solution in 5 ml of DMSO. After a contact time of 75 min, the reaction medium is diluted with a mixture of water and ethyl acetate. The aqueous phase is brought back to neutral pH and extracted with dichloromethane. After drying the organic phase over sodium sulfate and filtering, the residue is chromatographed on silica (gradient: CH$_2$Cl$_2$ 100 to CH$_2$Cl$_2$/MeOH 98:2) to give 52 mg of the expected product.

$^1$H NMR (200 MHz, CDCl$_3$): 0.05 ppm: s: 6H, 0.80 ppm: s: 9H, 5.30 ppm: s: 2H, 7.25-7.35 ppm: mt: 1H, 7.40-7.50 ppm: mt: 2H, 7.60 ppm: s: 1H, 7.70-7.85 ppm: mt: 1H, 7.90 ppm: bs: 1H, 8.0 ppm: d: 1H, 8.70 ppm: s: 1H, 8.75 ppm: bs: 1H.

Stage 2: 50 mg of the intermediate obtained in stage 1 and 33 mg of tetrabutylammonium fluoride in solution in 2 ml of THF are stirred at ambient temperature for 45 min. After hydrolyzing and diluting with the water/ethyl acetate mixture, the organic phase is washed with a saturated NaCl solution, dried over sodium sulfate and concentrated to dryness. The residue obtained is purified by preparative TLC (heptane/ethyl acetate 50:50) to give 16 mg of the expected product in the form of a yellow solid.

MH$^+$=479 $^1$H NMR (400 MHz, DMSO): 3.25 ppm: bs: 1H, 5.20 ppm: s: 2H, 7.45-7.55 ppm: mt: 1H, 7.60-7.70 ppm: mt: 2H, 8.00-8.15 ppm: mt: 3H, 8.90 ppm: bs: 1H, 9.0 ppm: bs: 1H, 10.90 ppm: bs: 1H.

Preparation of the Compound of Formula (II): 8-[3-((tert-butyl)dimethylsilanyl)prop-2-ynyl]-6-(2,6-dichlorophenyl)-2-methylsulfonyl-8H-pyrido[2,3-d]pyrimidin-7-one 8-[3-((tert-Butyl)dimethylsilanyl)prop-2-ynyl]-6-(2,6-dichlorophenyl)-2-methylsulfonyl-8H-pyrido[2,3-d]pyrimidin-7-one is prepared by following the procedure described in J. Med. Chem., 1998, 41, 3276-3292, starting from ethyl 4-chloro-2-(methylsulfanyl)pyrimidine-5-carboxylate and 3-((tert-butyl)dimethylsilanyl)prop-2-ynylamine, described below:

Stage 1: 22.02 g of di(tert-butyl) dicarbonate are added to 5 g of propargylamine dissolved in 50 ml of dichloromethane, cooled using an ice bath. After 1 h 30 at ambient temperature, the reaction medium is concentrated to give 15.5 g of the expected intermediate.

$^1$H NMR (200 MHz CDCl$_3$): 1.40 ppm: s: 9H, 2.20 ppm: t: 1H, 3.85-3.95 ppm: mt: 2H, 4.70 ppm: bs: 1H.

Stage 2: 43.8 ml of 2.5M n-butyllithium in THF are added to 8.5 g of the preceding protected amine, dissolved in 350 ml of THF and cooled to −70° C., under argon while maintaining a temperature of between −60° C. and −70° C. After a contact time of 30 min at −70° C., 17.02 g of tert-butyldimethylsilyl, in solution in 50 ml of THF, are added and the medium is stirred at −60° C. for 1 h. After returning to ambient temperature, 120 ml of 0.25M acetic acid are added and stirring is maintained for 1 h. The aqueous phase is then extracted with ethyl acetate and the combined organic phases are washed with a saturated NH$_4$Cl solution and with a saturated NaCl solution, dried over sodium sulfate and concentrated under vacuum to generate 15.02 g of the expected product in the form of a yellow solid.

$^1$H NMR (250 MHz, CDCl$_3$): 0.05 ppm: s: 6H, 0.90 ppm: s: 9H, 1.45 ppm: s: 9H, 3.70-3.80 ppm: mt: 2H, 4.60 ppm: bs: 1H.

Stage 3: 42 ml of TFA are added to 14.76 g of the derivative obtained in the preceding stage dissolved in 300 ml of dichloromethane. After 2 h at ambient temperature, the reaction medium is concentrated to give 15.73 g of 3-((tert-butyl)dimethylsilanyl)prop-2-ynylamine.

$^1$H NMR (250 MHz, DMSO): 0.05 ppm: s: 6H, 0.90 ppm: s: 9H, 3.70-3.80 ppm: mt: 2H, 8.25 ppm: bs: 2H.

EXAMPLE 14

(R/S)-2-(2-aminomethyl-2,3-dihydrobenzofuran-6-ylamino)-6-(2,6-dichlorophenyl)-8-methyl-8H-pyrido[2,3-d]pyrimidin-7-one Stage 1: 300 mg of compound of formula (III), described below, and 654 mg of compound of formula (II), 6-(2,6-dichlorophenyl)-8-methyl-2-methylsulfonyl-8H-pyrido[2,3-d]pyrimidin-7-one, are dissolved in 5 ml of THF. The reaction medium is heated at 120° C. in a sealed tube for 24 hours. After concentrating to dryness, the residue is chromatographed on silica (gradient: heptane 100 to heptane/ethyl acetate 50:50) to give 290 mg of the expected product.

$MH^+$=568 $^1$H NMR (200 MHz, DMSO): 1.40 ppm: s: 9H, 2.80-2.95 ppm: mt: 1H, 3.10-3.25 ppm: mt: 1H, 3.50 ppm: s: 3H, 3.65 ppm: bs: 2H, 4.70-4.90 ppm: mt: 1H, 7.10-7.60 ppm: mt: 7H, 7.90 ppm: s: 1H, 8.80 ppm: s: 1H, 10.25 ppm: s: 1H.

Stage 2: 2 ml of TFA are added, at ambient temperature, to 290 mg of the N-Boc intermediate dissolved in 5 ml of $CH_2Cl_2$. After a contact time of 2 h, the reaction medium is diluted with a dichloromethane/water mixture and basified up to a pH of 9 with $NaHCO_3$. The organic phase is washed with water and with a saturated NaCl solution, dried over sodium sulfate and concentrated to dryness. The residue is chromatographed on silica (gradient: $CH_2Cl_2$ 100 to $CH_2Cl_2$/MeOH 90:10 and then to $CH_2Cl_2$/MeOH/$NH_4OH$ 90:10:0.01) to give 35 mg of the expected product.

$MH^+$=468 $^1$H NMR (400 MHz, DMSO): 2.80 ppm: bs: 2H, 2.90-3.00 ppm: mt: 1H, 3.10-3.25 ppm: mt: 1H, 3.55 ppm: s: 3H, 4.75 ppm: bs: 1H, 7.15 ppm: d: 1H, 7.25 ppm: d: 1H, 7.40 ppm: s: 1H, 7.45-7.55 ppm: mt: 1H, 7.60-7.65 ppm: mt: 2H, 7.90 ppm: s: 1H, 8.85 ppm: s: 1H, 10.15 ppm: s: 1H.

Preparation of the Compound of Formula (III): (R/S)-2-(N-Boc-aminomethyl)-2,3-dihydrobenzofuran-6-ylamine The compound (III) is prepared according to the protocol described for the preparation of the compound (III) of example 12 starting from the compound ethyl (R/S)-6-amino-2,3-dihydrobenzofuran-2-carboxylate described in stage 2 of the preparation of the compound (III) of example 10.

EXAMPLE 15

2-(2-(aminomethyl)benzoxazol-5-ylamino)-6-(2,6-dichlorophenyl)-8-methyl-8H-pyrido[2,3-d]pyrimidin-7-one Stage 1: 687 mg of compound of formula (III), described below, and 2.506 g of compound of formula (II), 6-(2,6-dichlorophenyl)-8-methyl-2-methylsulfonyl-8H-pyrido[2,3-d]pyrimidin-7-one, are dissolved in 25 ml of THF. The reaction medium is heated at 110° C. in a sealed tube for 8 h. After concentrating to dryness, the residue is chromatographed on silica (gradient: dichloromethane 100 to dichloromethane/ethyl acetate 50:50) and 500 mg of the expected product are isolated in the powder form.

$MH^+$=567 $^1$H NMR (200 MHz): 1.40 ppm, s, 9H, 3.70 ppm, s, 3H, 4.40 ppm, d, 2H, 7.45 ppm, dd, 1H, 7.55-7.70 ppm, mt, 5H, 7.90 ppm, s, 1H, 8.35 ppm, bs, 1H, 8.90 ppm, s, 1H, 10.35 ppm, bs, 1H.

Stage 2: 5 ml of TFA are added, at ambient temperature, to 500 mg of the intermediate obtained above dissolved in 5 ml of $CH_2Cl_2$. After a contact time of 2 hours, the reaction medium is concentrated to dryness and then the residue is taken up in a mixture of water and ethyl acetate and basified up to pH 9 with $NaHCO_3$. The aqueous phase is extracted with ethyl acetate. The combined organic phases are washed with a saturated NaCl solution, dried over magnesium sulfate and concentrated to dryness. The residue is chromatographed on silica (gradient: $CH_2Cl_2$ 100 to $CH_2Cl_2$/MeOH 90:10) to give 244 mg of the expected product in the solid form.

$MH^+$=467 $^1$H NMR (200 MHz): 2.05 ppm, bs, 2H, 3.65 ppm, s, 3H, 3.90 ppm, s, 2H, 7.45 ppm, dd, 1H, 7.50-7.70 ppm, mt, 4H, 7.90 ppm, s, 1H, 8.30 ppm, bs, 1H, 8.80 ppm, s, 1H, 10.30 ppm, bs, 1H.

Preparation of the Compound of Formula (III): 2-(N-Boc-aminomethyl)benzoxazol-5-ylamine Stage 1: 14.95 g of 2-chlorotriethoxyethane are added to a solution of 9 g of 2-amino-4-nitrophenol in 50 ml of ethanol. After leaving overnight at 60° C., the reaction medium is concentrated to dryness and then the residue is taken up in ethyl acetate. The organic phase is washed with a 2N HCl solution, with water, with a saturated $NaHCO_3$ solution and finally with a saturated NaCl solution. After drying over magnesium sulfate and concentrating, the residue is taken up in diethyl ether and the precipitate formed is filtered off, washed with diethyl ether and dried to give 8.95 g of the expected product.

$MH^+$=213 $^1$H NMR (200 MHz): 5.15 ppm, s, 2H, 8.05 ppm, d, 1H, 8.40 ppm, dd, 1H, 8.70 ppm, d, 1H.

Stage 2: 6.83 g of sodium azide are added, under nitrogen and at ambient temperature, to a solution of 8.93 g of the chlorinated derivative obtained above in 135 ml of DMF. After a contact time of 30 minutes, the reaction medium is hydrolyzed on a mixture of water and ice and then ethyl acetate is added. After filtering in order to remove an insoluble material, the organic phase is washed with water and then with a saturated NaCl solution. After drying over magnesium sulfate and concentrating, 8.60 g of the expected product are isolated.

$^1$H NMR (200 MHz): 4.95 ppm, s, 2H, 8.05 ppm, d, 1H, 8.35 ppm, dd, 1H, 8.70 ppm, d, 1H.

Stage 3: 17.50 g of triphenylphosphine are slowly added to a solution of 8.60 g of the compound obtained in the preceding stage in 180 ml of ethyl acetate. After a contact time of 10 minutes, 7.1 ml of water are added and the reaction medium is heated at 60° C. for 1 hour. After returning to ambient temperature, the medium is diluted with ethyl acetate and the organic phase is washed with a saturated NaCl solution, dried over magnesium sulfate and concentrated. The residue is taken up in diethyl ether and then an insoluble impurity is removed by filtration. The filtrate is then acidified using ethereal hydrochloric acid and the hydrochloride of the expected product is filtered off, washed with diethyl ether and dried to give 2.70 g of the expected product.

$MH^+$=194 $^1$H NMR (200 MHz): 4.55 ppm, bs, 2H, 8.10 ppm, d, 1H, 8.40 ppm, dd, 1H, 8.70 ppm, d, 1H, 9.00 ppm, bs, 3H.

Stage 4: 3.77 ml of triethylamine and then, slowly, 3.34 g of di(tert-butyl) dicarbonate are added to a solution of 2.70 g of the amine obtained in the preceding stage in 30 ml of dichloromethane. After a contact time of 1 hour at ambient temperature, the reaction medium is diluted with dichloromethane and hydrolyzed with water. The organic phase is washed with a saturated $NaHCO_3$ solution, with water and finally with a saturated NaCl solution. After drying over magnesium sulfate and concentrating, the residue is taken up in heptane, filtered and again taken up in diethyl ether to give, after filtering and drying, 1.50 g of the expected product.

¹H NMR (200 MHz): 1.40 ppm, s, 9H, 4.50 ppm, d, 2H, 7.70 ppm, bt, 1H, 7.95 ppm, d, 1H, 8.30 ppm, dd, 1H, 8.60 ppm, d, 1H.

Stage 5: 3.34 g of zinc are added under nitrogen to 1 g of the compound obtained above in solution in 25 ml of THF, and then, while maintaining the temperature at approximately 0° C., 3.9 ml of acetic acid are slowly run in. After a contact time of 30 minutes at approximately 0° C. and returning to temperature, the reaction medium is diluted with ethyl acetate, filtered through celite and basified up to pH=9 with NaHCO$_3$. The organic phase is then washed with water and then with a saturated NaCl solution. After drying over magnesium sulfate and concentrating, 740 mg of 2-(N-Boc-aminomethyl)benzoxazol-5-ylamine are isolated.

MH$^+$=264 ¹H NMR (200 MHz): 1.40 ppm, s, 9H, 4.30 ppm, d, 2H, 5.05 ppm, bs, 2H, 6.60 ppm, dd, 1H, 6.75 ppm, d, 1H, 7.30 ppm, d, 1H, 7.55 ppm, bt, 1H.

TABLE I (I)

| Example No. | R1 | R2 | R3 | Ar$_1$ |
|---|---|---|---|---|
| 1 | —CH$_3$ | 2-Cl | 6-Cl | H$_2$N-CH$_2$-(benzo[1,3]dioxol-2-yl)-5-methyl (R/S) |
| 2 | —CH$_3$ | 2-Cl | 6-Cl | 5-methyl-1,3-dihydroisobenzofuran-1-yl |
| 3 | —CH$_3$ | 2-Cl | 6-Cl | 5-methyl-2,1,3-benzothiadiazol-4-yl |
| 4 | —CH$_3$ | 2-Cl | 6-Cl | 6-methyl-2,3-dihydrobenzofuran-3-yl |
| 5 (R) | —CH$_3$ | 2-Cl | 6-Cl | (R)-N,N-dimethyl-2-amino-3-(4-methylphenoxy)propanamide |
| 6 (S) | —CH$_3$ | 2-Cl | 6-Cl | (S)-N,N-dimethyl-2-amino-3-(4-methylphenoxy)propanamide |
| 7 | cyclopentyl | 2-Cl | 6-Cl | 5-methyl-2,1,3-benzothiadiazol-4-yl |
| 8 | —CH$_3$ | 2-Cl | 6-Cl | N-methyl-7-methyl-2,3-dihydro-1,4-benzodioxine-2-carboxamide (R/S) |

TABLE I-continued (I)

[Structure of formula (I): pyrido[2,3-d]pyrimidin-7(8H)-one core with HN-Ar₁ at 2-position, R1 on N8, and 6-aryl substituent bearing R2 and R3]

| Example No. | R1 | R2 | R3 | Ar₁ |
|---|---|---|---|---|
| 9 | —CH₃ | 2-Cl | 6-Cl | (aminomethyl)-2,3-dihydro-1,4-benzodioxine with methyl (R/S) |
| 10 | —CH₃ | 2-Cl | 6-Cl | N-ethyl 2,3-dihydrobenzofuran-2-carboxamide, 6-methyl (R/S) |
| 11 | —CH₃ | 2-Cl | 6-Cl | N-ethyl 2,3-dihydrobenzofuran-2-carboxamide, 5-methyl (R/S) |
| 12 | —CH₃ | 2-Cl | 6-Cl | 2-(aminomethyl)-5-methyl-2,3-dihydrobenzofuran (R/S) |
| 13 | —CH₂—C≡CH | 2-Cl | 6-Cl | 5-methyl-2,1,3-benzothiadiazole |
| 14 | —CH₃ | 2-Cl | 6-Cl | 2-(aminomethyl)-6-methyl-2,3-dihydrobenzofuran (R/S) |
| 15 | —CH₃ | 2-Cl | 6-Cl | 2-(aminomethyl)-5-methylbenzoxazole |

The compounds according to the invention have formed the subject of pharmacological trials which make it possible to determine their anticancer activity.

The compounds of formula (I) according to the present invention were tested in vitro on a sample group of tumor lines of human origin originating:

- from breast cancer: MDA-MB231 (American Type Culture Collection, Rockville, Md., USA, ATCC-HTB26), MDA-A1 or MDA-ADR (referred to as multidrug resistant MDR line, and described by E. Collomb et al. in Cytometry, 12(1), 15-25, 1991), and MCF7 (ATCC-HTB22),
- from prostate cancer: DU145 (ATCC-HTB81) and PC3 (ATCC-CRL1435),
- from colon cancer: HCT116 (ATCC-CCL247) and HCT15 (ATCC-CCL225),
- from lung cancer: H460 (described by Carmichael in Cancer Research, 47 (4), 936-942, 1987, and provided by the National Cancer Institute, Frederick Cancer Research and Development Center, Frederick, Md., USA),
- from glioblastoma: SF268 (described by Westphal in Biochemical & Biophysical Research Communications, 132 (1), 284-289, 1985, and provided by the National Cancer Institute, Frederick Cancer Research and Development Center, Frederick, Md., USA), from leukemia: CMLT1 (described by Kuriyama et al. in Blood, 74, 1989, 1381-1387, by Soda et al. in British Journal of Haematology, 59, 1985, 671-679, and by Drexler in Leukemia Research, 18, 1994, 919-927, and provided by DSMZ, Mascheroder Weg 1b, 38124, Brunswick, Germany), K-562 (described by Lozzio et al., J. Natl. Cancer Inst., 50, 535 (1973), by Lozzio et al., Blood, 45, 321 (1975), and provided by DSMZ, No. ACC 10) and KG1a (described by Koeffler in Blood, 56, 1988, 265-273).

The cell proliferation and viability were determined in a test using 3-(4,5-dimethylthiazol-2-yl)-5-(3-carboxymethoxyphenyl)-2-(4-sulfophenyl)-2H-tetrazolium (MTS) according to Fujishita T. et al., Oncology, 2003, 64 (4), 399-406. In this test, the mitochondrial ability of the living cells to convert MTS to a colored compound is measured after incubating for 72 hours a compound of formula (I) according to the invention. The concentrations of compound according to the invention which result in a 50% loss of cell proliferation and viability ($IC_{50}$) are between 1 nM and 10 µM, preferably between 1 nM and 1 µM, depending on the tumor line and the compound tested. For example, the product of example 1 has an $IC_{50}$ of 3 nM on $K_{562}$ cells and the product of example 2 has an $IC_{50}$ of 10 nM on MDA-MB231 cells. The product of example 8 has an $IC_{50}$ of 183 nM on MDA-MB231 cells and an $IC_{50}$ of 20.5 nM on K562 cells.

Thus, according to the present invention, it is apparent that the compounds of formula (I) bring about a loss of proliferation and viability of tumor cells. It is thus apparent that the compounds according to the invention have an anticancer activity and an activity in the treatment of other proliferative and inflammatory diseases, such as psoriasis, rheumatoid arthritis, osteoarthritis, multiple sclerosis, myasthenia, diabetes, Crohn's disease, transplantation of organs, restenosis, atherosclerosis, AIDS, for example, and also in diseases caused by the proliferation of vascular smooth muscle cells.

Thus, according to another of its aspects, a subject matter of the invention is medicaments which comprise a compound of formula (I) or an addition salt of the latter with a pharmaceutically acceptable acid or also a hydrate or a solvate of the compound of formula (I).

These medicaments are employed therapeutically, in particular in the treatment or prevention of diseases caused or exacerbated by the proliferation of cells and in particular tumor cells. These compounds are of use in the prevention and treatment of leukemia, solid tumors, both primary and metastatic, carcinomas and cancers.

These compounds are of use, as inhibitor of the proliferation of tumor cells, in the prevention and treatment of leukemia, in particular Acute Lymphocytic Leukemia (ALL), Acute Myeloid Leukemia (AML), Chronic Myeloid Leukemia (CML), Chronic Lymphocytic Leukemia (CLL), Myelodysplastic Syndromes (MDS), chloromas, plasmacytomas, T- or B-cell leukemias, non-Hodgkin's or Hodgkin's lymphomas, myelomas and other malignant hemopathies.

As inhibitor of the proliferation of tumor cells, these compounds are also of use in the prevention and treatment of solid tumors, both primary and metastatic, carcinomas and cancers, in particular: breast cancer; lung cancer; small intestine cancer, colon cancer and rectal cancer; cancer of the respiratory tract, oropharynx and hypopharynx; esophageal cancer; liver cancer, stomach cancer, bile duct cancer, gall bladder cancer, pancreatic cancer; cancers of the urinary tract, including kidney, urothelium and bladder; cancers of the female genital tract, including cancer of the uterus, cervix or ovaries, choriocarcinoma and trophoblastomic cancer; cancers of the male genital tract, including cancer of the prostate, seminal vesicles or testicles, and germ cell tumors; cancers of the endocrine glands, including cancer of the thyroid, pituitary gland or adrenal glands; cancers of the skin, including hemangiomas, melanomas or sarcomas, including Kaposi's sarcoma; tumors of the brain, nerves, eyes or meninges, including astrocytomas, gliomas, glioblastomas, retinoblastomas, neurinomas, neuroblastomas, schwannomas or meningiomas.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or a solvate of said compound, and also at least one pharmaceutically acceptable excipient.

Said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above or its possible salt, solvate or hydrate can be administered in the unit administration form, as a mixture with conventional pharmaceutical excipients, to animals and human beings for the prophylaxis or treatment of the above disorders or diseases.

Appropriate unit administration forms comprise oral forms, such as tablets, soft or hard gelatin capsules, powders, granules and oral solutions or suspensions, sublingual, buccal, intratracheal, intraocular or intranasal administration forms, forms of administration by inhalation, topical, transdermal, subcutaneous, intramuscular or intravenous administration forms, rectal administration forms and implants. Use may be made, for topical application, of the compounds according to the invention in creams, gels, ointments or lotions.

By way of example, a unit administration form of a compound according to the invention in the tablet form can comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropyl methylcellulose | 2.25 mg |
| Magnesium stearate | 3.0 mg |

The present invention also relates to therapeutic compositions comprising a compound according to the invention, in combination with an excipient which is pharmaceutically acceptable according to the method of administration chosen. The pharmaceutical composition can exist in the solid or liquid form or in the form of liposomes.

Mention may be made, among solid compositions, of powders, gelatin capsules or tablets. Oral forms can also include solid forms protected with regard to the acidic environment of the stomach. The carriers used for the solid forms are composed in particular of inorganic carriers, such as phosphates or carbonates, or of organic carriers, such as lactose, celluloses, starch or polymers. The liquid forms are composed of solutions, of suspensions or of dispersions. They comprise, as dispersive carrier, either water, on the one hand, or an organic solvent (ethanol, NMP or others) or mixtures of surface-active agents and of solvents or of complexing agents and of solvents, on the other hand.

The liquid forms will preferably be injectable and, for this reason, will have a formulation acceptable for such a use.

Acceptable routes of administration by injection include the intravenous, intraperitoneal, intramuscular and subcutaneous routes, the intravenous route being preferred.

The compounds of formula (I) above can be used at daily doses of 0.002 to 2000 mg per kilogram of body weight of the mammal to be treated, preferably at daily doses of 0.1 to 300 mg/kg. In man, the dose can preferably vary from 0.02 to 10 000 mg per day, more particularly from 1 to 3000 mg, according to the age of the subject to be treated or the type of treatment: prophylactic or curative.

There may be specific cases where higher or lower dosages are appropriate; such dosages do not depart from the scope of the invention. According to the usual practice, the dosage appropriate to each patient is determined by the physician according to the method of administration and the weight and the response of said patient.

The present invention, according to another of its aspects, also relates to a method for the treatment of the pathologies indicated above which comprises the administration, to a patient, of an effective dose of a compound according to the invention or one of its pharmaceutically acceptable salts or its hydrates or its solvates.

According to the present invention, the compound or compounds of formula (I) can be administered in combination with one (or more) anticancer active principle(s), in particular antitumor compounds, such as alkylating agents, such as alkylsulfonates (busulfan), dacarbazine, procarbazine, cloretazine, nitrogen mustards (chlormethine, melphalan, chlorambucil), cyclophosphamide or ifosfamide; nitrosoureas, such as carmustine, lomustine, semustine or streptozocin; antineoplastic alkaloids, such as vincristine or vinblastine; taxanes, such as paclitaxel or taxotere; antineoplastic antibiotics, such as actinomycin; intercalating agents, antineoplastic antimetabolites, folate antagonists or methotrexate; purine synthesis inhibitors; purine analogs, such as mercaptopurine or 6-thioguanine; pyrimidine synthesis inhibitors, aromatase inhibitors, capecitabine or pyrimidine analogs, such as fluorouracil, gemcitabine, cytarabine and cytosine arabinoside (Aracytin); brequinar; topoisomerase inhibitors, such as camptothecin or etoposide; anticancer hormonal agonists and antagonists, including tamoxifen; kinase inhibitors, imatinib and dasatinib; growth factor inhibitors; antiinflammatories, such as pentosan polysulfate, corticosteroids, prednisone or dexamethasone; antitopoisomerases, such as etoposide, anthracyclines, including doxorubicin, daunorubicin, idarubicin, bleomycin, mitomycin and mithramycin; anticancer metal complexes, platinum complexes, cisplatin, carboplatin or oxaliplatin; interferon-alpha, triphenyl thiophosphoramide or altretamine; antiangiogenic agents; thalidomide; immunotherapy adjuvants; or vaccines.

According to the present invention, the compounds of formula (I) can also be administered in combination with one or more other active principles of use in one of the pathologies indicated above, for example an agent for combating vomiting, pain, inflammation or cachexia. It is also possible to combine, with the compounds of the present invention, a radiation treatment. These treatments can be administered simultaneously, separately or sequentially. The treatment will be adapted by the practitioner according to the patient to be treated.

What is claimed is:
1. A compound corresponding to the formula (I):

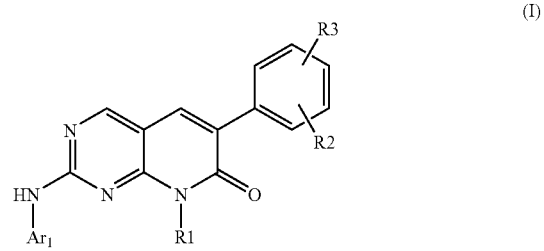

(I)

in which:
R1 is selected from the group consisting of: H, ($C_1$-$C_6$) alkyl, ($C_2$-$C_6$)alkenyl, ($C_2$-$C_6$)alkynyl, ($C_3$-$C_7$)cycloalkyl and ($C_3$-$C_7$)cycloalkyl ($C_1$-$C_6$)alkyl;

R2 and R3 are independently selected from the group consisting of: H, halogen, ($C_1$-$C_4$)alkyl, trifluoromethyl and ($C_1$-$C_4$)alkoxy;

$Ar_1$ represents a radical chosen from:

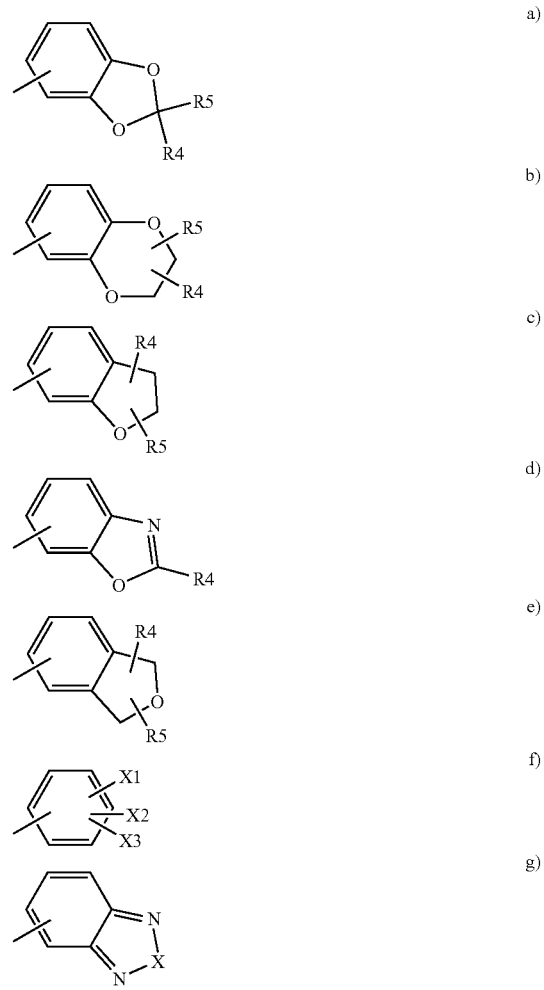

R5 is selected from the group consisting of: H, cyano, hydroxy($C_1$-$C_4$)alkyl, ($C_1$-$C_6$)alkoxy($C_1$-$C_4$)alkyl, —$(CH_2)_n$NR6R7, —$(CH_2)_m$$CO_2$R6, —$(CH_2)_m$CONHNR6R7, —$(CH_2)_m$CONR6R7, —$(CH_2)_m$CONR7OR8, —$(CH_2)_n$NR6COR7 and —$(CH_2)_n$NR6COOR7;

R4 is selected from the group consisting of: H, (C$_1$-C$_4$) alkyl and R5;

when Ar$_1$ takes the value a), then R4 and R5 are not two hydrogen atoms;

R6 and R7 are independently selected from the group consisting of: H, (C$_1$-C$_4$)alkyl, (C$_3$-C$_7$)cycloalkyl and (C$_3$-C$_7$)cycloalkyl(C$_1$-C$_4$)alkyl; R7 can also represent a tert-butoxycarbonyl or benzyloxycarbonyl group;

or R6 and R7, together with the nitrogen atom to which they are bonded, constitute an azetidinyl, pyrrolidinyl, piperidinyl, piperazinyl or morpholinyl radical;

R8 is selected from the group consisting of: H and (C$_1$-C$_4$) alkyl;

X is O or S;

X1 and X2 are independently selected from the group consisting of: H and —(C$_1$-C$_6$)alkyl-N((C$_1$-C$_6$)alkyl)$_2$;

when one of X1 and X2 is other than H, then X3 is selected from the group consisting of: hydroxyl and (C$_1$-C$_6$) alkoxy;

when X1 and X2 are H, then X3 is selected from the group consisting of: —(CH$_2$)$_n$—CH(NHR9)—CO—R10, —O—(CH$_2$)$_n$—CH(NHR9)—CO—R10 and —NHSO$_2$—(C$_1$-C$_6$)alkyl;

R9 is selected from the group consisting of: H, t-butyloxycarbonyl, benzyloxycarbonyl and (C$_1$-C$_6$)alkyl;

R10 is selected from the group consisting of: hydroxyl, (C$_1$-C$_6$)alkoxy and —NR11R12;

R11 and R12 are independently selected from the group consisting of: H and (C$_1$-C$_6$)alkyl; or R11 and R12, together with the nitrogen atom to which they are bonded, constitute an azetidinyl, pyrrolidinyl, piperidinyl, piperazinyl or morpholinyl radical;

m represents 0, 1, 2 or 3;

n represents 1, 2 or 3;

or a pharmaceutically acceptable salt, hydrate or solvate thereof.

2. The compound of formula (I) according to claim 1, wherein Ar$_1$ represents a radical chosen from:

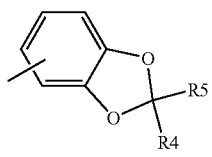

a)

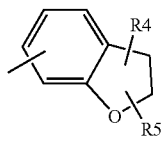

c)

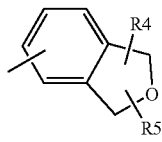

d)

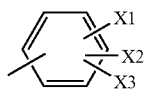

e)

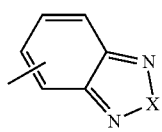

f)

in which R4, R5, X1, X2, X3 and X are as defined in claim 1;

or a pharmaceutically acceptable salt, hydrate or solvate thereof.

3. The compound of formula (I) according to claim 1, wherein R$_1$ represents a methyl group;

or a pharmaceutically acceptable salt, hydrate or solvate thereof.

4. The compound of formula (I) according to claim 1, wherein R$_1$ represents a cyclopentyl group;

or a pharmaceutically acceptable salt, hydrate or solvate thereof.

5. The compound of formula (I) according to claim 1, wherein R$_1$ represents a —CH$_2$—C≡CH group;

or a pharmaceutically acceptable salt, hydrate or solvate thereof.

6. The compound of formula (I) according to claim 1, wherein R2 and R3 are two chlorine atoms in the 2 and 6 positions;

or a pharmaceutically acceptable salt, hydrate or solvate thereof.

7. The compound of formula (I) according to claim 1, wherein Ar$_1$ represents the following radical:

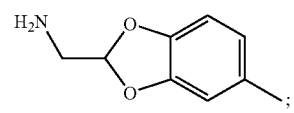

or a pharmaceutically acceptable salt, hydrate or solvate thereof.

8. The compound of formula (I) according to claim 1, wherein Ar$_1$ represents the following radical:

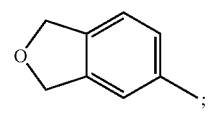

or a pharmaceutically acceptable salt, hydrate or solvate thereof.

9. The compound of formula (I) according to claim 1, wherein Ar$_1$ represents the following radical:

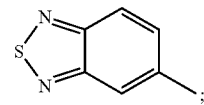

or a pharmaceutically acceptable salt, hydrate or solvate thereof.

10. The compound of formula (I) according to claim 1, wherein Ar$_1$ represents the following radical:

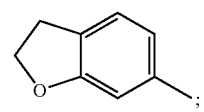

or a pharmaceutically acceptable salt, hydrate or solvate thereof.

11. The compound of formula (I) according to claim 1, wherein Ar₁ represents the following radical:

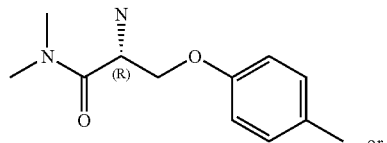

or

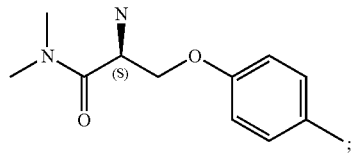

;

or a pharmaceutically acceptable salt, hydrate or solvate thereof.

12. The compound of formula (I) according to claim 1, wherein Ar₁ represents the following radical:

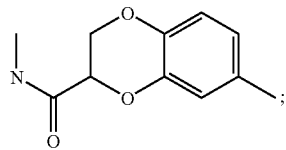

;

or a pharmaceutically acceptable salt, hydrate or solvate thereof.

13. The compound of formula (I) according to claim 1, wherein Ar₁ represents the following radical:

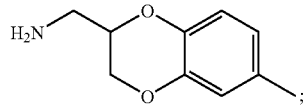

;

or a pharmaceutically acceptable salt, hydrate or solvate thereof.

14. The compound of formula (I) according to claim 1, wherein Ar₁ represents the following radical:

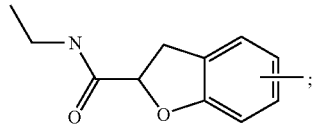

;

or a pharmaceutically acceptable salt, hydrate or solvate thereof.

15. The compound of formula (I) according to claim 1, wherein Ar₁ represents the following radical:

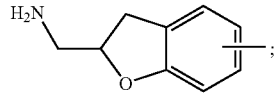

;

or a pharmaceutically acceptable salt, hydrate or solvate thereof.

16. The compound of formula (I) according to claim 1, wherein Ar₁ represents the following radical:

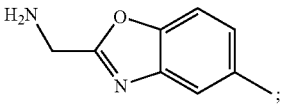

;

or a pharmaceutically acceptable salt, hydrate or solvate thereof.

17. The compound according to claim 1 selected from the group consisting of:
   6-(2,6-dichlorophenyl)-2-[(1,3-dihydro-5-isobenzo-furanyl)amino]-8-methyl-8H-pyrido[2,3-d]pyrimidin-7-one;
   (R/S)-2-[[2-(aminomethyl)-1,3-benzodioxol-5-yl]amino]-6-(2,6-dichlorophenyl)-8-methyl-8H-pyrido[2,3-d]pyrimidin-7-one;
   2-(2,1,3-benzothiadiazol-5-ylamino)-6-(2,6-dichlorophenyl)-8-methyl-8H-pyrido[2,3-d]pyrimidin-7-one;
   6-(2,6-dichlorophenyl)-2-[(2,3-dihydro-6-benzofuranyl)amino]-8-methyl-8H-pyrido[2,3-d]pyrimidin-7-one;
   (2R)-2-amino-3-[4-[[6-(2,6-dichlorophenyl)-7,8-dihydro-8-methyl-7-oxopyrido[2,3-d]pyrimidin-2-yl]amino]phenoxy]-N,N-dimethylpropanamide; and
   (2S)-2-amino-3-[4-[[6-(2,6-dichlorophenyl)-7,8-dihydro-8-methyl-7-oxopyrido[2,3-d]pyrimidin-2-yl]amino]phenoxy]-N,N-dimethylpropanamide;
   or a pharmaceutically acceptable salt, hydrate or solvate thereof.

18. The compound according to claim 1 selected from the group consisting of:
   (R/S)-N-methylamide of 7-[6-(2,6-dichlorophenyl)-8-methyl-7-oxo-7,8-dihydropyrido[2,3-d]pyrimidin-2-ylamino]-2,3-dihydrobenzo[1,4]dioxin-2-carboxylic acid;
   (R/S)-2-(2-aminomethyl-2,3-dihydrobenzo[1,4]dioxin-6-ylamino)-6-(2,6-dichlorophenyl)-8-methyl-8H-pyrido[2,3-d]pyrimidin-7-one;
   (R/S)-N-ethylamide of 6-[6-(2,6-dichlorophenyl)-8-methyl-7-oxo-7,8-dihydropyrido[2,3-d]pyrimidin-2-ylamino]-2,3-dihydrobenzofuran-2-carboxylic acid;
   (R/S)-N-ethylamide of 5-[6-(2,6-dichlorophenyl)-8-methyl-7-oxo-7,8-dihydropyrido[2,3-d]pyrimidin-2-ylamino]-2,3-dihydrobenzofuran-2-carboxylic acid;
   (R/S)-2-(2-aminomethyl-2,3-dihydrobenzofuran-5-ylamino)-6-(2,6-dichlorophenyl)-8-methyl-8H-pyrido[2,3-d]pyrimidin-7-one;
   (R/S)-2-(2-aminomethyl-2,3-dihydrobenzofuran-6-ylamino)-6-(2,6-dichlorophenyl)-8-methyl-8H-pyrido[2,3-d]pyrimidin-7-one;
   2-(2,1,3-benzothiadiazol-5-ylamino)-8-cyclopentyl-6-(2,6-dichlorophenyl)-8H-pyrido[2,3-d]pyrimidin-7-one;
   2-(2,1,3-benzothiadiazol-5-ylamino)-6-(2,6-dichlorophenyl)-8-(prop-2-ynyl)-8H-pyrido[2,3-d]pyrimidin-7-one; and
   2-(2-(aminomethyl)benzoxazol-5-ylamino)-6-(2,6-dichlorophenyl)-8-methyl-8H-pyrido[2,3-d]pyrimidin-7-one.

19. The compound according to claim 1, wherein the compound is in the:
   non-chiral form, or
   racemic form, or
   form enriched in a stereoisomer, or
   form enriched in an enantiomer.

20. A process for the preparation of a compound of formula (I) according to claim 1, comprising reacting a compound of formula (II):

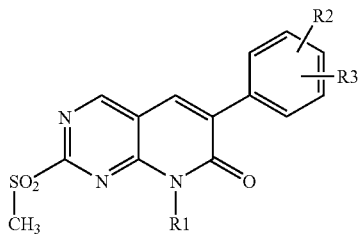

in which R1, R2 and R3 are as defined for formula (I) in claim 1, with an amine of formula Ar'$_1$NH$_2$ (III) in which Ar'$_1$ represents Ar$_1$, as defined for formula (I) in claim 1.

21. A pharmaceutical composition comprising a compound of formula (I) according to claim 1, or a pharmaceutically acceptable salt, a hydrate or a solvate of said compound, and at least one pharmaceutically acceptable excipient.

22. The pharmaceutical composition of claim 21, further comprising one or more other anticancer active principle(s).

* * * * *